(12) United States Patent
Schultz

(10) Patent No.: US 12,788,548 B2
(45) Date of Patent: *Nov. 10, 2026

(54) COMPLIANT SCAFFOLD

(71) Applicant: Brent Schultz, Scottsdale, AZ (US)

(72) Inventor: Brent Schultz, Scottsdale, AZ (US)

(*) Notice: Subject to any disclaimer, the term of this patent is extended or adjusted under 35 U.S.C. 154(b) by 1098 days.

This patent is subject to a terminal disclaimer.

(21) Appl. No.: 17/941,875

(22) Filed: Sep. 9, 2022

(65) Prior Publication Data

US 2023/0000608 A1 Jan. 5, 2023

Related U.S. Application Data

(63) Continuation-in-part of application No. 17/222,868, filed on Apr. 5, 2021, now Pat. No. 12,588,985, which is a continuation-in-part of application No. 17/021,802, filed on Sep. 15, 2020, now Pat. No. 10,966,832, which is a continuation-in-part of application No. PCT/US2020/013729, filed on Jan. 15, 2020.

(60) Provisional application No. 63/391,251, filed on Jul. 21, 2022, provisional application No. 63/254,033, filed on Oct. 8, 2021, provisional application No. 63/242,462, filed on Sep. 9, 2021, provisional application No. 62/792,867, filed on Jan. 15, 2019.

(51) Int. Cl.
*A61F 2/00* (2006.01)
*A61F 2/12* (2006.01)

(52) U.S. Cl.
CPC .............. *A61F 2/0077* (2013.01); *A61F 2/12* (2013.01); *A61F 2230/006* (2013.01)

(58) Field of Classification Search
CPC .. A61F 2/12; A61F 2/0077; A61F 2230/0039; A61F 2230/0052; A61F 2230/0058
See application file for complete search history.

(56) References Cited

U.S. PATENT DOCUMENTS

| | | | |
|---|---|---|---|
| 8,049,059 | B2 | 11/2011 | Bleyer et al. |
| 8,680,360 | B2 | 3/2014 | Greener et al. |
| 10,548,776 | B2 | 2/2020 | Greener et al. |

(Continued)

FOREIGN PATENT DOCUMENTS

| | | | |
|---|---|---|---|
| WO | 9706837 | A1 | 2/1997 |
| WO | 2020139544 | A2 | 7/2020 |

*Primary Examiner* — Christopher D. Prone
(74) *Attorney, Agent, or Firm* — Invention To Patent Services; Alex Hobson

(57) ABSTRACT

A compliant scaffold incorporates a plurality of elongated apertures that form a geometric pattern enabling biaxial expansion or contraction. An elongated aperture has a pair of nodes located on opposing sides of the aperture and between a pair of antinodes located on the extended and opposing ends of the elongated aperture. A geometric pattern may have various geometric shapes, or tiles, between the plurality of apertures. The geometric tiles have a bounded perimeter formed by the plurality of elongated apertures. A substantial portion of the elongated apertures may be configured with the antinodes proximal to one of said pair of nodes of a separate elongated aperture; wherein the antinodes are closer to one of the pair of nodes than to any other antinode. This unique arrangement of the elongated apertures may be formed in biological material in vivo or ex vivo.

15 Claims, 37 Drawing Sheets

(56) References Cited

U.S. PATENT DOCUMENTS

| | | | | |
|---|---|---|---|---|
| 10,966,832 | B2 * | 4/2021 | Schultz | A61F 2/12 |
| 2004/0260315 | A1 * | 12/2004 | Dell | A61F 2/0063<br>623/23.72 |
| 2013/0211519 | A1 | 8/2013 | Dempsey | |
| 2015/0165636 | A1 | 6/2015 | Woodroof | |
| 2015/0202343 | A1 | 7/2015 | Woodroof | |
| 2016/0256259 | A1 | 9/2016 | Wirth et al. | |
| 2020/0222177 | A1 | 7/2020 | Paydar et al. | |
| 2021/0220112 | A1 * | 7/2021 | Schultz | A61F 2/2846 |

* cited by examiner

COMPLIANT SCAFFOLD

CROSS REFERENCE TO RELATED APPLICATIONS

This application is a continuation in part of U.S. patent application Ser. No. 17/222,868, filed on Apr. 5, 2021 and currently pending, which is a continuation in part of U.S. patent application Ser. No. 17/021,802 filed on Sep. 15, 2020 and issued as U.S. Pat. No. 10,966,832 on Apr. 6, 2021, which is a continuation in part of PCT application No. PCT/US2020/013729, filed on Jan. 15, 2020, which claims the benefit of priority to U.S. provisional patent application No. 62/792,867, filed on Jan. 15, 2019, and this application claims the benefit of priority to U.S. provisional patent No. 63/242,462, filed on Sep. 9, 2021, U.S. provisional patent No. 63/254,033, filed on Oct. 8, 2021 and to U.S. provisional patent No. 63/391,251, filed on Jul. 21, 2021; the entirety of each application listed in this Cross Reference To Related Applications is hereby incorporated by reference herein.

BACKGROUND OF THE INVENTION

Field of the Invention

The invention relates to a compliant scaffold having a pattern of elongated apertures to enable biaxial elongation and contraction for compliance, and methods of forming said biological compliant scaffold, ex vivo or in vivo.

Background

There are a large number and types of scaffolds that are implanted into the body or topically applied to the skin. Skin grafts are commonly used for burn victims and for cosmetic surgeries. It is common to mesh these scaffolds to expand them, thereby increasing the area of coverage offered by a limited resource, and improving their compliance. Current mesh designs allow for the scaffold to be elongated in one direction at the expense of length in the perpendicular direction. This mono-direction elongation results in stress being placed on the surrounding tissue, wrinkles in the graft and surrounding tissue and in some cases rupture or tears. It significantly limits compliance when attempting to cover or modify three dimensional structures.

SUMMARY OF THE INVENTION

The invention is directed to a biological compliant scaffold having a pattern of elongated apertures to enable biaxial elongation and contraction and methods of forming said biological compliant scaffold both ex vivo or in vivo. The pattern of elongated apertures includes nodes and antinodes that enables bi-lateral expansion through expansion of the apertures and rotation of tiles configured therebetween. This renders the biological compliant scaffold compliant around complex shapes including round or curved surfaces. An exemplary biological compliant scaffold is expandable or moldable and can encourage selective contraction in specific areas; all of which systematically change the shape of the biological compliant scaffold. Altering the compliance and plasticity of a biological compliant scaffold is accomplished by introducing a plurality of elongated apertures that form a geometric pattern that enables biaxial expansion. This may be in vivo modification of living tissue including, but not limited to, skin, tendon, muscle, vessel, bone, and the like, ex vivo modification of living tissue such as sundry harvested grafts including, but not limited to, skin, bone or tendon, or modification of implantable biological devices such as plates, acellular dermal matrix, allograft, xenograft and the like. The invention is directed to a biological compliant scaffold and method of forming said biological compliant scaffold by creating the elongated apertures in a pattern as detailed herein in vivo or ex vivo.

A pattern of elongated apertures, in a closed or expanded state, or combination thereof can be formed in vivo on a bone or may be formed in a bone graft external to the body and then implanted.

A biological compliant scaffold, as used herein includes graft or biologic materials implanted or attached to biological material or tissue, and ex vivo grafts wherein biological material comprises a plurality of elongated apertures as described herein. A biological compliant scaffold may have no blood supply and be implanted to be revitalized, may be a flap wherein blood supply is left intact. A biological compliant scaffold may be tissue from the patient or from a donor that is configured with a plurality of elongated apertures, it may be tissue that is altered ex vivo with a plurality of elongated apertures or a combination of both. A biological compliant scaffold may be a non-biological material such as a fastener, screw, plate and the like and may be made out of biologically compatible materials, such metal, metal alloys, stainless steel, titanium, nitinol, bioresorbable materials, polymeric materials such as fluoropolymers and in particular polytetrafluoroethylene. Biological, as used herein, includes tissue or materials that are biologically compatible for implantation such as certain metals and alloys, polymers and the like.

A compliant scaffold made of metal may be made out of shape memory alloy such as a composite of nickel-titanium, nitinol. This material is used in stents and stent grafts and in some cases the vasculature may be non-uniform or branched and a metal with a pattern of elongated apertures as described herein may be used for compliance of the stent. Other metal implantable applications may include intravascular filters, hernia patch material, bone plates, fasteners and the like. Stents may be used in the intravascular system, gastro-intestinal system or liver system, for example. A stent may be a self-expanding stent that is made out of a shape memory material or may be a balloon expandable stent. A stent may have be a bare stent or may be part of a stent-graft, comprising a graft material coupled to the stent.

A compliant scaffold may be made out of a bioresorbable material that may be used within the body that overtime is absorbed. A bioresorbable material may comprise a pattern of elongated apertures therethrough and may configured with other implantable materials, such as a stent or graft.

A compliant scaffold, such as one made of metal, plastic, fiber board, films, architectural or building materials, for example, may be used in as a building scaffolding for concrete or other materials that are later applied thereto or coated thereon or therethrough. The compliant metal scaffold may be placed and shaped over a curved or irregular shaped structure and then the building material, such as concrete may be applied. The compliant metal scaffold may be configured over an expandable or inflatable structure that is then inflated to cause the compliant scaffold to conform to the expanded shape and subsequently, a building material, such as concrete, may be applied. The expandable structure may then be retracted and removed, leaving a structure that is curved or irregularly shaped.

A compliant scaffold made be used in garments or apparel applications and may be made out of an elastomeric material or may be coupled with an elastomeric material to enable the apparel article, such as a garment to conform to an individual body shape and retract when taken off. An elastomeric material may be applied to, imbibed into a compliant scaffold material having the plurality of elongated apertures. A compliant scaffold may be made out of an elastomeric material, such as a sheet or fabric. Elastomeric apparel articles are common for both athletic activities and for general fashion. Undergarments, leggings and even jeans incorporate elastomeric materials to provide form fitting garments and the compliant scaffold may be incorporated with these garments.

An elastomeric material is a material that can be deformed, such as by stretching by a deforming load, and will substantially return to pre-deformed state, upon removal of a deforming load. An elastomeric sheet is a planar piece of material that can be stretched and substantially return to original dimensions, such as within about 10% or preferably within about 5%, within about one hour of removal of a extension force; wherein the stretch is performed over no more than 2 minutes and is no more than a 30% elongation and wherein the elastomeric material is not held in stretched state for more than a minute.

A compliant scaffold made be used in garments or apparel applications, such as for molds or supports for shoes, hats or helmets, or for brassieres wherein a specific supporting contour would be desired. A compliant scaffold for apparel applications may be made of metal, elastomeric material, plastic, foams and the like. A compliant scaffold may be a metal sheet or plastic sheet with the apertures formed therethrough. In the brassiere application, the compliant scaffold support may be provided with the apertures closes or partially open and then the geometry of a particular person may further form and open or close the apertures. An exemplary compliant graft may be used in avant-garde apparel to form shapes that form part of the unique design. An exemplary compliant graft may also be used for draperies or other applications where fluid movement and conformability are desired.

An exemplary compliant scaffold may be configured as an enclosure, such as a duffle bag or purse such that the enclosure can expand and conform to accommodate items therein. The enclosure may comprise an elastomeric component that enables the expanded compliant scaffold to retract after removal of the items therein.

An exemplary compliant scaffold may be configured as a rapid splint or support structure for medical purposes. A sheet of compliant scaffold formed of a plastic or metal, for example, may be shaped and formed around an appendage to retain the limb in a desired orientation and prevent movement. A sheet or roll of conformable material may be cut and formed in the field for emergency applications. An exemplary compliant scaffold may be configured as a C-collars for cervical spine stabilization, for example.

An exemplary compliant scaffold may be configured as a structural support for a structure, such as a building, a dwelling, roof and the like. The compliant scaffold may be shaped in situ to form the compliant and shaped structure and may have a secondary material applied to further support the structure, such as cement or a resin.

In an exemplary embodiment, the elongated apertures comprise a pair of nodes centrally located on opposing sides of the aperture and between a pair of antinodes, wherein the antinodes are configured on opposing ends of the elongated aperture. The geometric pattern comprises a plurality of geometric shapes, or tiles, between the plurality of apertures. The geometric shapes or tiles have a bounded perimeter formed by the plurality of elongated apertures. An exemplary biological compliant scaffold, has a substantial portion of the elongated apertures that are configured with the antinodes proximal to one of said pair of nodes of a separate elongated aperture; wherein the antinodes are closer to one of the pair of nodes than to any other antinode; wherein the node and antinode are considered a node, antinode pair. This unique arrangement of the elongated apertures produces a biological compliant scaffold material that can be biaxially expanded. During expansion of the biological compliant scaffold, the first and second nodes separate from each other while the antinodes approach each other to form an arrangement of tessellated apertures. The arrangement of the elongated apertures and tiles therebetween enables biaxial expansion with tiles rotating. Adjacent tiles that are connected through a node antinode pair counter rotate and those adjacent tiles not connected by a node antinode may pair co-rotate. This combination of tile rotation and aperture expansion enables a generally uniform biaxially expansion.

The position to apertures relative to one another can be used to alter the properties of the compliant scaffold, including stiffness and percent elongation or expansion. The first means of doing this is to maintain the basic node antinode relationship between adjacent elongated apertures but increase the space between the apertures which effectively also increases the distance between node and antinode pairs. The second method of altering the properties of the compliant graft requires altering the place of interaction between nodes and antinodes along the elongated aperture. Moving the point of interaction of nodes to adjacent antinodes may change the expansion ratio and allow fine tuning the stiffness and expansile properties of the compliant scaffold for a specific application.

An exemplary biological compliant scaffold may be beneficial in a wide array of applications, including skin grafts, bone grafts, cardiac patches or grafts, hernia patches or grafts, organ grafts, vascular graft and stent grafts, for example. A graft may be a donor graft comprising material such as skin, bone or tissue from a donor patient, or from a donor site of the patient being treated, or may be a constructed graft, which may comprise organic donor material or layers and additional material or layers. A constructed scaffold may be synthetic scaffold made from non-donor materials such as bioresorbable material that resorb into the body over time. An exemplary scaffold material may be an in vivo scaffold made by creating the plurality of apertures and geometric pattern in the tissue directly, such as with the use of lasers. For example, a laser may be used to create a geometric pattern in skin by making the plurality of slits or apertures directly in the skin of a patient. Furthermore, an exemplary biological compliant scaffold formed in vivo in skin by imprinting the skin tissue with the plurality of apertures as described herein, is a way of programming the tissue to expand in areas where the scaffold is not expanded and contract in areas where the scaffold is expanded. Thus far, skin tissue has been made into an unexpanded biological compliant scaffold which allows for the scaffolds or tissue to expand. This can however be done in reverse; Imprinting tissue with a fully expanded scaffold and removing the material from the apertures, or selectively burning/treating said tissue within the apertures with an instrument such as a laser. This would allow for the scaffold to contract rather than expand. Such a scaffold would be useful in shortening bones to address limb length discrepancies or in common operations such as the ulnar shortening osteotomy. Furthermore, such a fully expanded scaffold could be imprinted in skin which would encourage the skin to tighten. This application may be useful in body contouring procedures including breast lifts or facial aesthetic procedures such a facelifts and neck-lifts. This technique is not limited to a scaffold made of skin. The plurality of apertures may be microscopic in scale, such as less than a millimeter in length, a micron or less to sub-micron range, or less than a micron in length. The apertures may also be larger for some applications, such as a few millimeters to a millimeter.

It is also possible to imprint tissue with a differentially expanded scaffold which would precisely direct selective expansion and contraction on the same surface. An exemplary biological compliant scaffold may comprise a portion with a plurality of apertures configured to promote expansion or extension of the biological scaffold and may comprises a second portion configured to contract. A first portion of a biological compliant scaffold may comprise expanded apertures, such as expanded elongated apertures and a second portion may comprise a plurality of apertures that are not expanded. A first portion of a biological compliant scaffold may comprise unexpanded apertures, such as unexpanded elongated apertures and a second portion may comprise a plurality of apertures that are partially or fully expanded. The geometric pattern of apertures may comprise regions of elongated apertures in different degrees of expansion to promote reconfiguration of the biological material or scaffold.

Exemplary biological compliant scaffold skin grafts may be used to repair damaged skin, such as from burns, chemical damage, cuts or abrasions, for example. An exemplary biological compliant scaffold skin grafts may provide compliance in highly elongated areas, including the elbows, knees and the like. As mentioned, biological compliant scaffold skin grafts may be used in cosmetic procedures such as cleft palate surgeries and the like.

An exemplary biological compliant scaffold bone graft may be used to aid in the restructure of bone. In an Ilizarov technique, the two ends of the bone are slowly distracted and an in-vivo biological compliant scaffold bone may be created along a portion of the bone to improve the compliance of the bone and increase the rate of distraction. Alternatively, an in-vivo biological compliant scaffold bone may be used along a portion of the bone, instead of or in conjunction with a full thickness osteotomy to improve the compliance of the bone. Improved compliance may enable more strain of the for a given amount of stress or force on the biological compliant scaffold. The Ilizarov technique is used where one bone is shorter than another through injury, or birth. In some cases, the Ilizarov technique is used for cosmetic reasons, such as to make a person taller. In some cases, this technique may not just augment but actually obviate the need for the Ilizarov technique. These applications fall under the general category of osteogenic distraction that involves making complete osteotomies in bone to be expanded. By transforming the same bone into a biologic scaffold as described, using this plurality of apertures, such distraction techniques mat not require full osteotomies, or separation of the bone being altered, but rather a plurality of smaller partial osteotomies that may greatly reduce distraction times, and increase safety by creating inherently more stable expansion constructs.

An exemplary biological compliant scaffold bone graft may be used in a Cranioplasty technique to repair abnormal skull shapes. An ex-vivo biological compliant scaffold bone graft may be produced in a skull using a laser, bone scalpel or other suitable method to produce apertures through the skull or through a portion of the skull. This ex-vivo biological compliant scaffold bone may allow expanding or contracting of the cranial vault to treat pediatric growth malformations. In addition, this ex-vivo biological compliant scaffold method may be a more effective treatment to treat increased intra cranial pressure in adults from such conditions as hydrocephalus, intracranial mass or acute or chronic trauma. It is also possible to create a compliant meshed scaffold from the cranial vault in vivo without extricating the skull or removing it from its blood supply. Such techniques may augment current so called “strip craniectomy” procedures.

An exemplary biological compliant scaffold of bone may be a bone graft, osseous free flap, or vascularized in vivo bony structure having elongated apertures formed therein ex vivo or in vivo for osteoplasty. Osteoplasty is the branch of surgery concerned with bone shaping, repair, or bone grafting. It is the surgical alteration or reshaping of bone and may be used to relieve pain associated with metastatic bone disease. An in vivo bone biological compliant scaffold may include a pattern of elongated apertures in a closed configuration and/or in an expanded configuration, wherein the elongated apertures are an expanded scaffold. For example, for ulna shortening, a bone may be configured with a pattern of elongated apertures in an open state to encourage the bone to shorten. Note that an osteoplasty utilizing a pattern of elongated apertures, as described herein, may be used to shorten, lengthen, twist or otherwise remodel bone. An exemplary biological compliant scaffold may be a bone graft or flap having elongated apertures formed ex vivo or in vivo respectively for osteoplasty.

These scaffolds may be part of computer guided osteotomy with pre bent plates for corrective osteotomies. Currently these osteotomies are a series of pre-planned full thickness bone cuts that then allow for the bones to be reconfigured in a predetermined way and affixed to a prebent plate, which may be computer aided in terms of determination of the pattern of osteotomies and/or control of a cutting implement, such as a laser, drill, saw, or knife to create the pattern of osteotomies. The biologic scaffold can render bones compliant and moldable, using a predetermined pattern of apertures, expanded, partially expanded, unexpanded or a combination thereof, obviating or reducing the need for full thickness osteotomies, and can be a part of the computer guided osteotomy and reshaping process. This is particularly valuable in face/mandible/skull reconstruction or correction and complex limb reconstruction/corrections.

An exemplary biological compliant scaffold has a plurality of elongated apertures that are linear apertures extending between a pair of antinodes, or from a first antinode to a second antinode. Exemplary elongated apertures have a length to width ratio in a non-elongated state of about two or more, about three or more, about five or more and any range between and including the ratios provided. The length of the apertures may be microscopic such as less than a millimeter in length, including in the micron range to a micron or less, or sub-micron range. An exemplary biological compliant scaffold may consist of linear elongated apertures which may all be microscopic as defined herein. The length of the apertures may be larger however, such in the range of millimeters to about a millimeter.

The density of the plurality of elongated apertures configured in a pattern to produce geometric shapes or tiles may vary depending on the application, wherein the spacing between them, or inter-aperture distance between the apertures, is configured depending on the type of material and the amount of conformability desired. The repeat distance is the distance between adjacent elongated apertures from the same feature of the two adjacent elongated apertures, such as from a particular node to the same node on an adjacent elongated aperture. The inter-aperture distance and/or the repeat distance between adjacent elongated apertures may be microscopic in some applications such as less than a millimeter in length, including in the micron range to a micron or less, or sub-micron range. The size of the elongated apertures and/or the spacing and/or the repeat distance in one or more directions may change over the surface of a compliant scaffold to enable various amounts of conformance or elongation for irregular shaped surfaces, such as a breast or a support for in a brassiere.

The distance between nodes and antinodes of a compliant scaffold may be selectively altered, thereby changing the relative size of living hinges of those node antinode pairs that have been changed, which will also selectively alter the compliance of the meshed material or tiles between the apertures. Differential conformance within the same mesh allows for said mesh to alter the shape of the compliant object, material or tissue that the mesh contains. A compliant scaffold may therefore expand differentially depending on the specific geometry of the apertures, length of apertures, and distance between the apertures and particularly the distance between the node-antinode pairs. For instance, a sphere made of compliant of spongy material could be enveloped in a mesh, where selective alterations were made regarding certain node-antinode pairs. These selective areas may be more or less compliant. In this way the mesh may be pre-programmed to alter the shape of the matter it covers or contains. In such a state, the sphere (possessing spherical symmetry) could be made to adopt any number of other shapes with fewer planes of symmetry such as a teardrop shape, cylinder, cone, pyramid (radial symmetry) or even more complex shapes with fewer or no planes of symmetry.

The geometric pattern of a compliant scaffold may be applied to alter the structure or function of any underlying compliant material it is applied to, or an object may be pre-fabricated with the material of interest already enveloped in this mesh and that new composite object of underlying material and mesh may be used, applied or implanted wholesale. Such objects, once installed could then undergo further alterations to the mesh to fine tune its structure and function.

An exemplary compliant scaffold comprises a control geometric pattern of apertures having at least a portion of the apertures arranged in a non-uniform geometric pattern of apertures that is configured preferentially to expand in a pre-defined manner, wherein the geometric pattern is more easily expanded or expands to a greater degree in a first portion of the compliant scaffold and wherein a second portion of the compliant scaffold is harder to expand or expands to a lesser degree than said first portion. A control geometric pattern of apertures may have different length apertures, different spaces between apertures, different spacing between node-antinode pairs, different shaped and dimension tiles and the like. The changes in the pattern may be gradual to produce smooth transitions across an expanded surface.

An exemplary compliant scaffold configured for cosmetic implant, such as for breast augmentation, may have a non-uniform geometric pattern of apertures that is configured preferentially expand in a pre-defined manner, wherein the geometric pattern is more easily expanded or expands to a greater degree in a first portion of the compliant scaffold and wherein a second portion of the compliant scaffold is harder to expand or expands to a lesser degree than said first portion. A compliant scaffold with a non-uniform geometric pattern of apertures may be configured in a breast implant directly or into a cover configured to extend around a breast implant, or may be coupled to the tissue such that the tissue is preferentially expanded by the breast implant to form a desired shape. This same concept may be applied to other cosmetic implant areas, such as the face including the cheek or lips, butt, arms, calves, legs and the like.

An exemplary biological compliant scaffold for breast augmentation and in particular to retain a breast implant may be made out of a biological material as described herein, a material that can be implanted into the body, which may include synthetic materials including polymers, such as fluoropolymers, metals such as titanium, stainless steel or nitinol, or acellular dermis xenograft, (pigskin) for example. The biological compliant scaffold may be attached to the tissue to produce differential compliance of the tissue in a desired shape. The biological compliant scaffold may be configured as a pouch that extends around a portion of a first and second side of a breast implant or may form an enclosure. The biological compliant scaffold may comprise an attachment flange or a portion around a perimeter that may be used to couple the biological compliant scaffold to the tissue. A surgeon may couple the biological compliant scaffold, such as a pouch to the tissue and then insert the breast implant. The pouch may then be closed such as by stitching the opening of the pouch closed.

An exemplary biological compliant scaffold for cosmetic or reconstructive lifting procedures such as breast lifts, face lifts, body lifts and may be made out of a biological material as described herein, a material that can be implanted into the body, which may include synthetic materials including polymers, such as fluoropolymers, metals such as titanium, stainless steel or nitinol, or acellular dermis xenograft, (pigskin) for example. The biologic compliant scaffold may be attached to the tissue to produce differential compliance of the tissue in a desired shape. The biologic scaffold in breast lifting (mastopexy) or reduction procedures may be directly attached to the breast mound, to be formed or lifted, once the skin flaps have been developed and the breast mound dissected. Once attached to the chest, the compliant scaffold can be placed in the breast mound on any desired position on the chest (allowing for lift) and in any desired shape.

This concept of preferentially expanding compliant scaffolds with a non-uniform geometric pattern of apertures may be applied in a wide array of applications including, but not limited to, garments, containers, bags, purses, support structures such as hammocks, canopies, and the like. In a garment application, the garment or an undergarment may comprise a layer of material that is a compliant scaffold with a non-uniform geometric pattern of apertures. The garment may then preferentially expand to produce a desired shape, such as to raise the buttocks or in lift and shape the breasts.

An exemplary biological compliant scaffold comprises a plurality of elongated apertures configured in a pattern to produce geometric shapes or tiles. In an exemplary embodiment, a substantial portion of the elongated apertures, such as 50% or more and preferably 80% or more, are arranged orthogonally to each other, wherein a first elongated aperture is orthogonal to a second elongated aperture configured on a first antinode end of said first elongated aperture. In an exemplary embodiment, a biological compliant scaffold consists essentially of, such as at least 90% or more, elongated apertures that are arranged orthogonally to each other. A geometric pattern having elongated apertures that are arranged orthogonally to each other includes a first elongated aperture having a first antinode end that is proximal to a first node of a second elongated aperture, and the length axis of the first and second elongated apertures are substantially orthogonal to each other, or within about 20 degrees or orthogonal.

In an exemplary embodiment, a biological compliant scaffold comprises a plurality of cross-shaped apertures, wherein a length axis of the first elongated aperture extends through a first node of the second elongated aperture. A cross-shaped apertures comprises four antinodes on the extended ends of the two intersecting elongated apertures. An exemplary cross-shaped aperture has a length axis of a first elongated aperture that extends centrally through the second elongated aperture, such as within about 20% of the center of the length of the second elongated aperture. The length of the two elongated apertures of the cross-shaped aperture may be substantially the same or within about 20% of each other. A symmetric cross-shaped aperture comprises two elongated apertures of substantially the same length that intersect with each other centrally, as defined herein.

In an exemplary embodiment, a biological compliant scaffold comprises plurality of Y-shaped apertures, having three separate extension that extend from a central point. An exemplary Y-shaped aperture comprises three extensions that are substantially the same length and these three extensions may extend substantially an equidistant circumferentially from each other, wherein each extends from the center point about 120 degrees apart, such as within about 100 to 140 degrees.

An exemplary biological compliant scaffold comprising two pairs of nodes configured between antinodes along said elongated aperture. This type of elongated aperture forms a rectangle aperture upon expansion of the nodes from each other. A first pair of nodes forms one side of the rectangular aperture with a first antinode configured therebetween and the second pair of nodes forms a second and opposing side of the rectangle with the second antinode therebetween.

An exemplary biological compliant scaffold comprises a geometric pattern of elongated apertures and geometric shapes wherein a substantial portion of the elongated apertures are arranged in a I-configuration. In an I-configuration, a first elongated aperture is substantially orthogonal, within about 20 degrees of orthogonal, to a second elongated aperture configured on the first antinode end of said first elongated aperture and wherein said first elongated aperture is substantially orthogonal to a third elongated aperture configured on the second antinode end of said first elongated aperture.

An exemplary biological compliant scaffold comprises a geometric pattern of elongated apertures and geometric shapes wherein the geometric shape has a plurality of corners and wherein each of said plurality of corners are bound by a node of separate elongated apertures. An exemplary biological compliant scaffold comprises a geometric pattern of elongated apertures and geometric shapes wherein the geometric shape is a rectangle and wherein the corners of the rectangle are bound by a node of four separate elongated apertures. An exemplary biological compliant scaffold comprises a geometric pattern of elongated apertures and geometric shapes wherein the geometric shape is a triangle and wherein the corners of the triangle are bound by a node of three separate elongated apertures, which may be a side of an adjacent triangular geometric shape. An exemplary biological compliant scaffold comprises a geometric pattern of elongated apertures and geometric shapes and may comprise a single geometric shape, or two or more geometric shapes. An exemplary biological compliant scaffold comprises a geometric pattern of elongated apertures and geometric shapes and may consists essentially of a single geometric shape, such as a rectangle or triangle.

A cutting template may be used to indicate the geometric pattern of elongated apertures for cutting in the biological material which may be in vivo or ex vivo. In an exemplary embodiment and cutting template is translucent or transparent and placed over tissue in vivo, such over a fracture in bone or over a wound in tissue. A medical profession may then form the pattern by cutting through the template into the bone or tissue, and may cut only around the fracture or the wound. A cutting template may have an adhesive on one side for adhering to the biological material. In ex vivo biological material, a cutting template may be applied and used manually or may guide an automated cutting implement, such as an automatically controlled laser cutter.

A biological scaffold may have elongated apertures having one or more blanks, wherein the blanks are removed material that may be in a particular shape. A blank may be configured along the elongated aperture, such as being proximal to the extended end of an extension or proximal to an antinode configured on an extended end of the elongated aperture or may be configured along the length of the elongated aperture. A blank may be configured at the intersection of extensions of the elongated aperture or at a bi-node or tri-node, for example. A blank may be circular or oval in shape, or may be triangular or polygonal in shape, such as a rectangle, square, pentagon and the like. The blank may be centered over the elongated aperture or extension of the elongated aperture or may have a linear side the extends along the elongated aperture or extension thereof. A blank may be circular in shape and be centered over the tri-node, for example, or may be triangular in shape with one side of the triangle extending along the elongated aperture and terminating at an antinode on the end of the elongated aperture.

The compliant scaffold may be a solid versus a sheet or layer of material having a thickness that is a fraction of the planar dimension of the compliant scaffold. A sheet type compliant scaffold has a thickness that is no more than 10% or a planar dimension and may be no more than 5% of a planar dimension, or even no more than 2% or even 1% of a planar dimension. A standard A4 sheet of paper has a thickness that is less than $1/100^{th}$ the planar dimension, for example. A solid compliant scaffold on the other hand has a thickness that is at least 10% and in most cases 25% or more any planar dimension. A cube for example has a thickness that is equal to the planar side dimensions, or about 100% of the thickness. A solid compliant scaffold may have a geometric pattern of apertures that extend through the solid from a first side, through the compliant scaffold to another side, such as an opposing side when the apertures are straight line apertures. A solid compliant scaffold may be a polyhedron having planar surfaces or may have curved surfaces or be a combination of both. A solid compliant scaffold may be a rod or have a general rod shape, such as a bone. The through apertures may extend through the bone to allow for remodeling the bone and/or extending or lengthening the bone. A solid compliant scaffold may be a polyhedron and apertures may extend symmetrically through the polyhedron from a first side to an opposing second side. This type of solid three-dimensional compliant scaffold with elongated apertures may allow elongating within necking or narrowing of the compliant scaffold and may provide a more easily restructured or deformable compliant scaffold. The apertures may only extend a portion of a depth into a solid and three-dimensionally shaped compliant scaffold, such as a polyhedron or a three-dimensional compliant scaffold that having curved surfaces including a rod, cylinder or a sphere. Apertures may extend into a solid or three-dimensional compliant scaffold and intersect with each other to produce interconnected wedges of the three-dimensional compliant scaffold that can move independently from other wedges. This may enable expansion and/or contraction of the three-dimensional compliant scaffold. A three-dimensional compliant scaffold has an outer surface extending in three-dimensions to form a shape.

A compliant scaffold may have apertures, as described herein including, but not limited to, I-shaped apertures, Y-shaped apertures and cross-shaped apertures that have a width or gap along the apertures. This gap between the nodes may be formed in the compliant scaffold, such as by molding, or may formed by removing compliant scaffold material within the aperture.

The depth, length, type, arrangement, scale of apertures in a compliant scaffold including sheet type compliant scaffold and especially three-dimensional compliant scaffold may be configured to provide mechanical properties for a particular application. Also, the apertures may be changes from one area of the compliant scaffold to another to provide a change in mechanical properties, such as modulus to enable effective deformation, such as compression, expansion or bending of the compliant scaffold. For example, a bone may have a first area with apertures that produce a more compliant bone than a second area and this first area may allow the bone to flex and bend to prevent excessive stress and possible breaking of the bone during healing, for example.

Definitions

An adjacent tile portion is a tile portion connect to another tile portion by a connection portion.

A substantial portion as used herein means at least 50% or more and preferably 80% or more.

In vivo, as used herein with respect to formation of geometric pattern of elongated apertures, means forming said geometric pattern of elongated apertures in biological tissue native to the patient and in or a part of the patient's body; in vivo may be part of a surgical procedure.

Ex vivo, as used herein with respect to formation of geometric pattern of elongated apertures, means forming said of geometric pattern of elongated apertures in biological material outside of a patient's body.

Any of the geometric patterns of apertures described herein for biological material and/or apparel may be used in any compliant scaffold material, such as biological material as defined herein, apparel material, such as fabric or films, woven materials, construction materials, and the like. Likewise, the various embodiments of the biological compliant scaffold material may also be used in apparel material, such as fabric or films, woven materials, construction materials, and the like.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 22 shows a geometric pattern of I-shaped apertures to form a biological compliant scaffold and the expanded biological compliant scaffold.

FIG. 23 shows a geometric pattern of I-shaped apertures to form a biological compliant scaffold and the expanded biological compliant scaffold.

FIG. 24 shows a geometric pattern of I-shaped apertures to form a biological compliant scaffold and the expanded biological compliant scaffold.

FIG. 25 shows a geometric pattern of I-shaped apertures having two antinodes between a first and second node.

FIG. 26 shows a geometric pattern of Y-shaped apertures.

FIG. 27 shows a Y-shaped aperture having nodes between the intersection of three legs of the Y-shaped aperture and an tri-node at the intersection.

FIG. 28 shows a geometric pattern of skewed shaped apertures.

FIG. 29 shows a geometric pattern including cross-shaped apertures between skewed shaped apertures.

Figure 1:
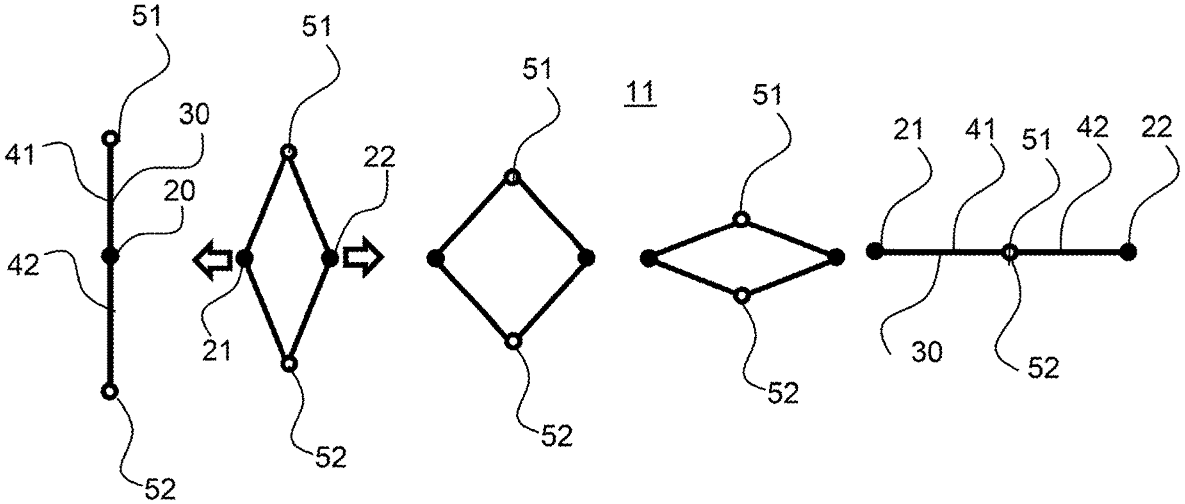
FIG. 1 PRIOR ART
FIG. 1 shows an exemplary elongated aperture having a pair of nodes configured on opposing extended ends of the elongated aperture and a pair of antinodes configured centrally between the extended ends and on opposing sides of the elongated aperture.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Throughout the figures nodes in an elongated aperture are depicted as circles and antinodes are depicted as black circles.

A biological compliant scaffold, as used herein, is a material that is biologically compatible and that is compliant to enable expansion or contraction along the plurality of apertures and includes, but is not limited to, ex vivo biologically material such as bone, muscle, skin, organ tissue and the like, biologically tissue or material from a secondary organism, as well as synthetic biological material including polymeric graft materials, such as fluoropolymers, bioresorbable materials, metal and metal alloys including titanium, stainless steel, shape memory metal alloys including, NiTi alloys or Nitinol and the like. A biological compliant scaffold may be formed ex vivo by the formation of the plurality of elongated apertures in tissue or bone for example.

As shown throughout the figures, a node is represented as an black circle and an antinode is represented as a open circle.

As shown in FIG. 1, an exemplary graft 11 comprises an elongated aperture 30 comprising a pair of nodes 20, or node pair configured centrally between two antinodes 51, 52. A pair of nodes is an arrangement of two nodes next to each other on opposing sides of an elongated aperture. This pair of nodes comprises node 21 and 22. The elongated aperture has a first extension 41 extending from the node pair 20 to the first antinode 51 and a second extension 42 extending from the node pair to the second antinode 52. As the biological compliant scaffold is elongated the nodes 21, 22, of the elongated aperture 30 separate to form a diamond. As the biological compliant scaffold is stretched further the nodes separate further and the antinodes contract toward each other whereby the nodes become antinode and the antinodes become nodes. As the biological compliant scaffold is elongated further, the antinodes approach one another and the nodes are fully extended apart. This simple elongated aperture produces a maximally expanded square aperture when nodes and antinodes are equidistant. Further expansion of the nodes in the same relative direction leads to contraction of this maximum open area of the aperture with the antinodes moving closer to each other until in essence the nodes have become antinodes and the antinodes have become nodes. This is a reason why apertures not connected by node/antinode pairs contract in one direction when expanding in another.

Figure 2:
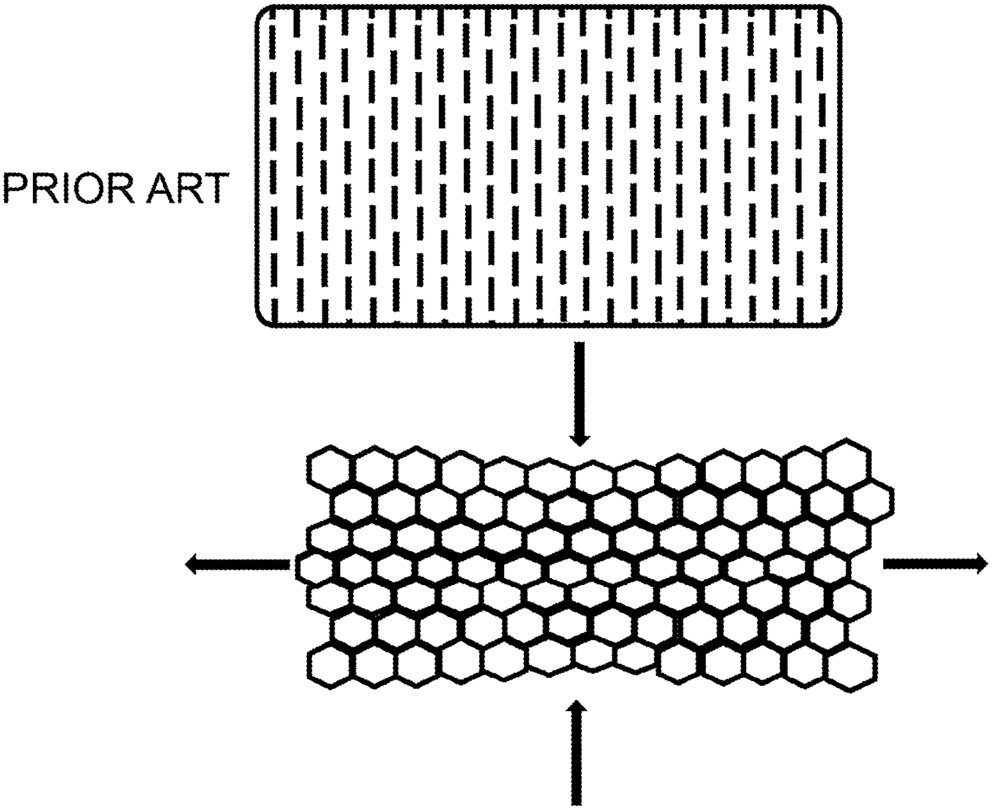
FIG. 2 shows an exemplary graft having an arrangement of elongated apertures that results in contraction of the graft when elongated.
Figure 3:
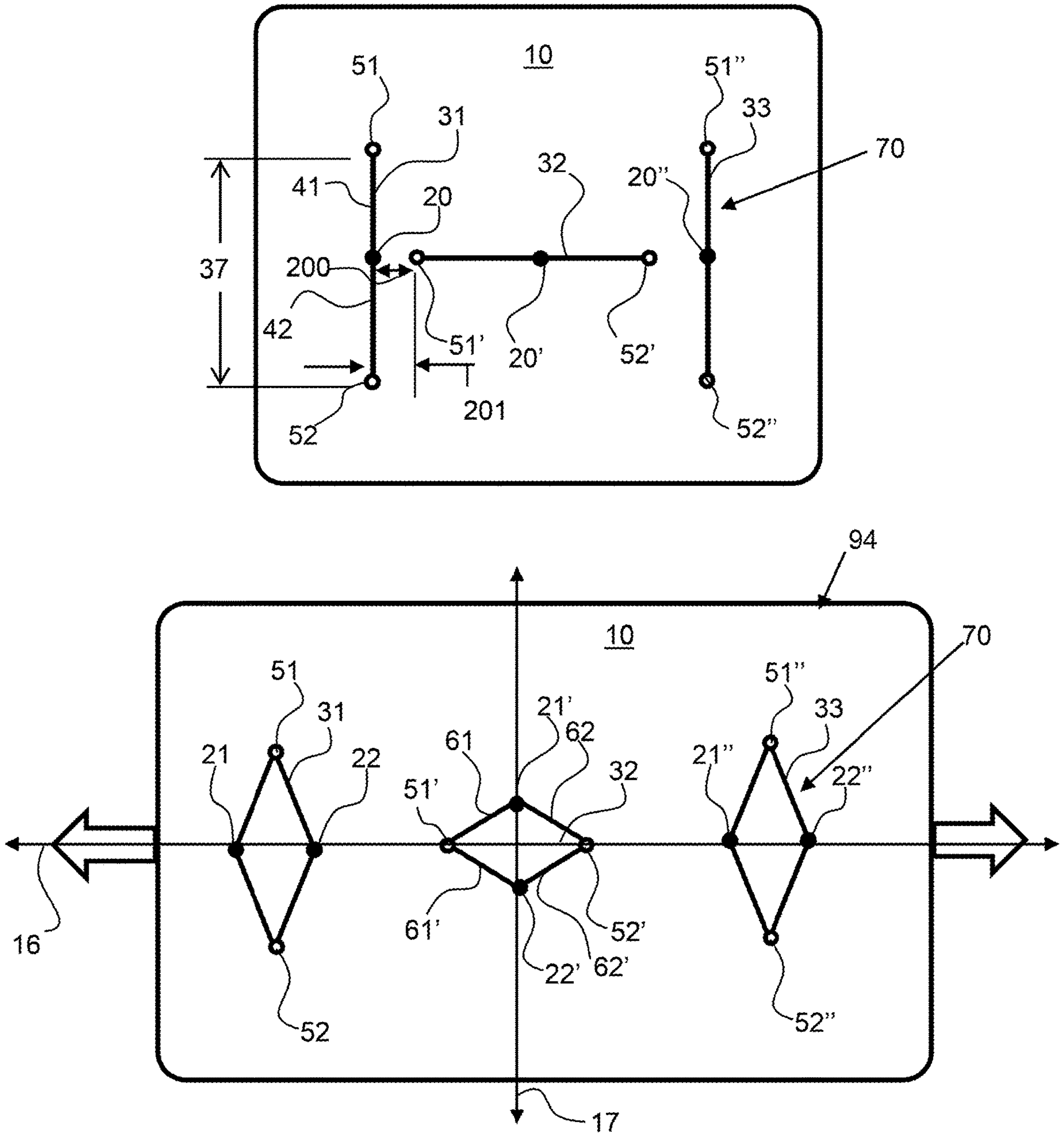
FIG. 3 shows an exemplary biological compliant scaffold having elongated apertures configured with the nodes of a first elongated aperture proximal to the antinodes of an adjacent elongated aperture.

As shown in FIG. 2, a graft having an arrangement of apertures aligned with each other can be elongated but this causes contraction in the opposing direction. The nodes separate and the antinodes contract causing the graft material to neck in, or contract, in a direction perpendicular to the direction of elongation. FIG. 3 shows an exemplary compliant scaffold 10 with an exemplary geometric pattern of I-shaped elongated apertures 70 comprising elongated apertures 31, 32, and 33, each having nodes 21, 22 configured between a pair of antinodes 51, 52 in a linear elongated aperture. The top figure shows the biological compliant scaffold without tension or elongation. The bottom figure shows the graft material being elongated, as indicated by the bold arrows. As the material is elongated, the nodes 21, 22 of the two outer elongated apertures 31 and 33, separate in the direction of the elongation, or the elongation axis 16. The nodes of the center elongated aperture 32 also separate as the sides 61, 62, and 61', 62' around the antinodes 21' and 22', respectively, separate in the elongation axis. As the sides separate, the nodes 21', 22' also separate in the cross-elongation axis 17. The configuration of the antinodes of the center elongated aperture 32 proximal to the pairs of nodes 20, 20' and 20", of the outer elongated apertures 31, 33, causes this more uniform elongation of the biological compliant scaffold material without necking or contraction in the cross-elongation axis. The bottom compliant scaffold 10 is an expanded scaffold 94. The inter-aperture distance 201 between adjacent elongated apertures is shown between the first elongated aperture 31 and the second elongated aperture 32. This gap distance 200 may be a distance between a node and the closest antinode, which may be uniform or modified over a geometric pattern of apertures to produce differential compliance, as shown in later figures. As described herein, this space may be preferably on the same scale as the elongated aperture length 37. When the gap distance is greater, the compliant scaffold may be stiffer or present a higher modulus for expansion of the scaffold. Also, the percent expansion may be reduced as a function of the area of the compliant scaffold. The compliant scaffold material between the antinode and node may act as a hinge, such as a living hinge, for the scaffold or tile and may include a different material of additional material from the rest of the compliant scaffold material. An elastomeric material may be configured as a hinge between the elongated apertures. A hinge may be configured between the elongated apertures including a mechanical or elastomeric hinge. As shown in FIG. 3, there is a significant distance between the antinode of one elongated aperture and the node of an adjacent elongated aperture. These distances can be adjusted from angstrom scale to any practical length. Increasing the node/adjacent antinode distance effectively decreases the ratio of expansion and decreases compliance. Such an adjustment leads to a stiffer mesh (with a higher young's modulus) that may be better matched to the young's modulus of nearby or connected materials or structures. Decreasing this distance makes the mesh more conformable.

Figure 4:
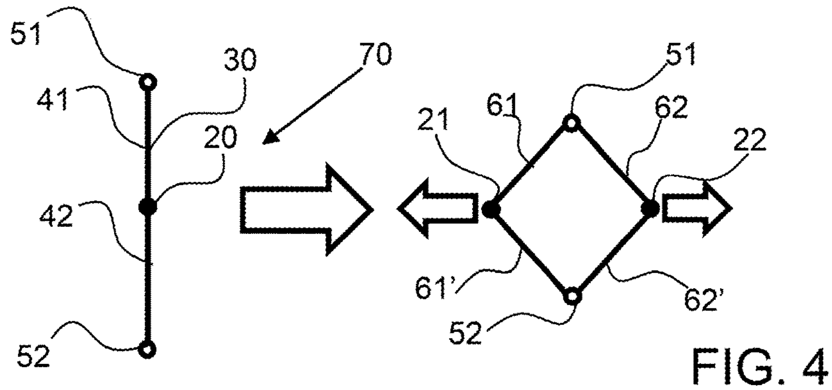
FIGS. 4 to 9 show a plurality of elongated aperture configurations with nodes configured between antinodes.

FIG. 4 shows an exemplary linear elongated aperture 30 having a pair of nodes 20 configured centrally along the aperture and pair of antinodes 51, 52 configured on opposing ends of the aperture. A first antinode 51 is configured at the extended end of a first extension 41 from the pair of nodes and a second antinode 52 is configured at the extended end of a second extension 42 from the pair of nodes. As shown in the expanded version of the elongated aperture, a square shaped opening or aperture may be formed from the elongated aperture when elongated as indicated by the bold arrows. The two sides 61, 62, and 61', 62' of the elongated aperture between the nodes and antinodes form the sides of the rectangle.

Figure 5:
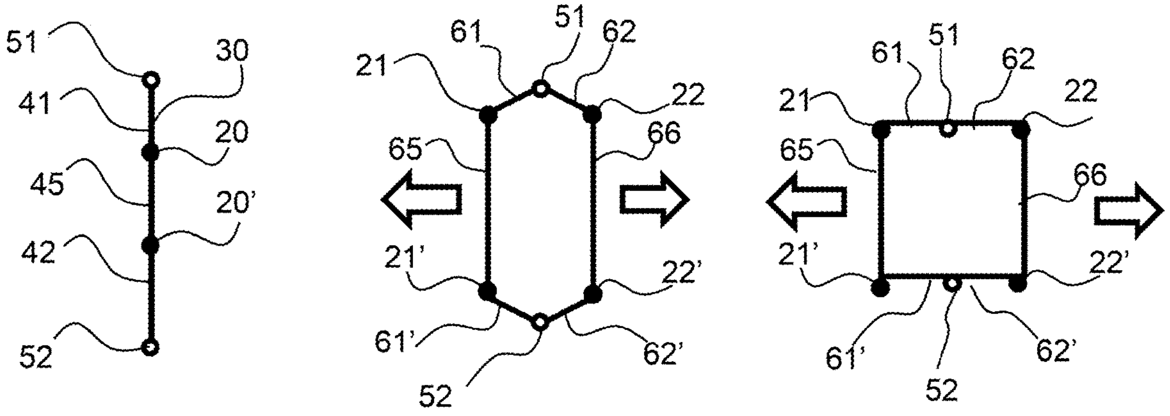

As shown in FIG. 5, an exemplary elongated aperture 30 has two pairs of nodes 20, 20' configured between two opposing antinodes 51, 52. Again, this is a linear elongated aperture having a first extension 41 from the first pair of nodes 20 to the first antinode 51 and a second extension 42 from the second pair of nodes 20' to the second antinode 52. A node extension 45 extends between the two pairs of nodes 20, 20'. As the elongated aperture is elongated, a hexagon shaped aperture is formed initially that may form into a square or rectangle, depending on the lengths of the extensions and node extensions. A first side 61 and a second side 62 of the aperture is formed on either side of the antinode 51 and a first side 61' and a second side 62' of the aperture is formed on either side of the antinode 52. A first node side 65 and second node side 66 are formed between the two pairs of nodes, or more specifically, between nodes 21 and 21' and nodes 22 and 22', respectively.

Figure 6:
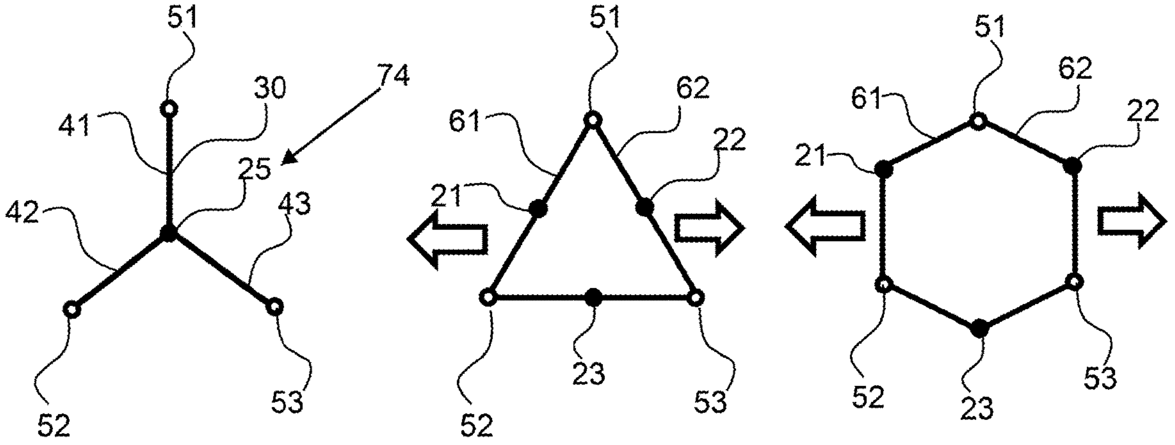

As shown in FIG. 6, an exemplary Y-shaped aperture 74 has three antinodes configured around a centrally configured tri-node 25 which includes node 21, 22 and 23. Each of the antinodes 51, 52, 53 is configured at the extended end of an extension that extends from the tri-node 25. A first antinode 51 is configured at the extended end of a first extension 41 from the tri-node, a second antinode 52 is configured at the extended end of a second extension 42 from the tri-node and a third antinode 53 is configured at the extended end of a third extension 43 from the tri-node. The three extensions are configured at a substantially equal circumferential distance from each other, or about 120 degrees apart plus or minus 20 degrees and more preferably within 10 degrees of 120 degrees. As this elongated aperture is elongated, as indicated by the bold arrows, the nodes 21, 22, and 23 separate from each other to form a triangular shaped aperture. As the elongated aperture is elongated further, a hexagonal shaped aperture is formed. This elongated aperture provides a high level of compliance in multiple directions. A side extends between each antinode and the two adjacent nodes, such as sides 61 and 62 extending between antinode 51 and nodes 21 and 22.

Figure 7:
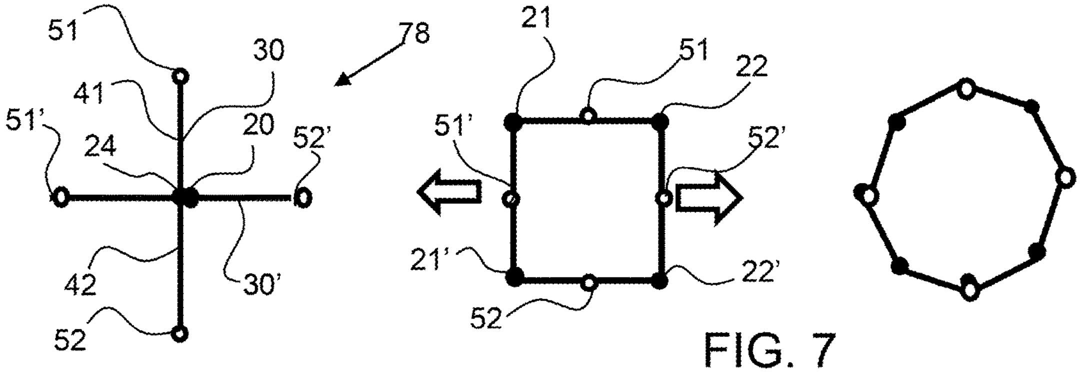

As shown in FIG. 7, a cross-shaped aperture comprises two elongated apertures that intersect at a node 20, or quad node 24. The quad node 24, being a configuration of four nodes located proximal to each other, separates into these four nodes, 21, 21', 22, and 22' to form a rectangle upon expansion, as indicated by the bold arrows in the center figure. The antinodes 51, 52, 51', 52' are configured between the nodes. Further expansion results in a polygon having eight surfaces. The nodes are indicated by solid small circles while the antinodes are indicated by small circles.

Figure 8:
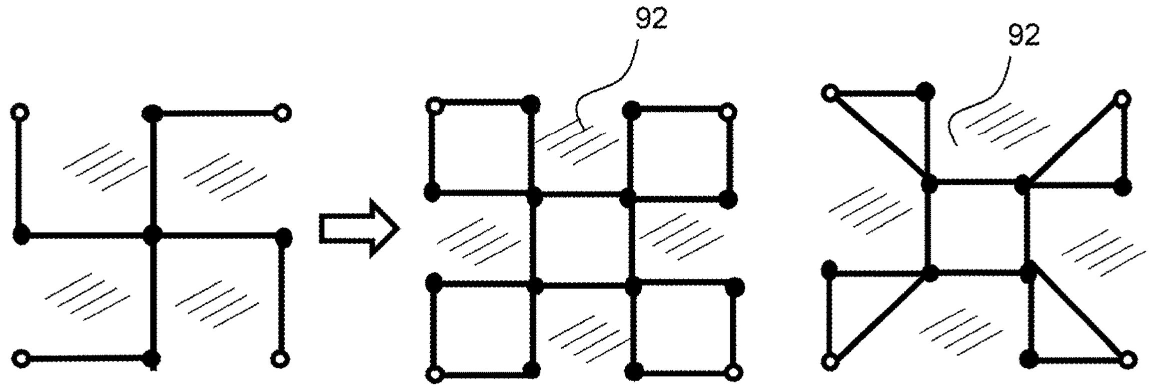

As shown in FIG. 8, a more complex aperture comprises a generally cross-shaped aperture with extensions from each of the extended ends of the cross. This complex shaped aperture produces tiles 92 within the quadrants of the apertures.

Figure 9:
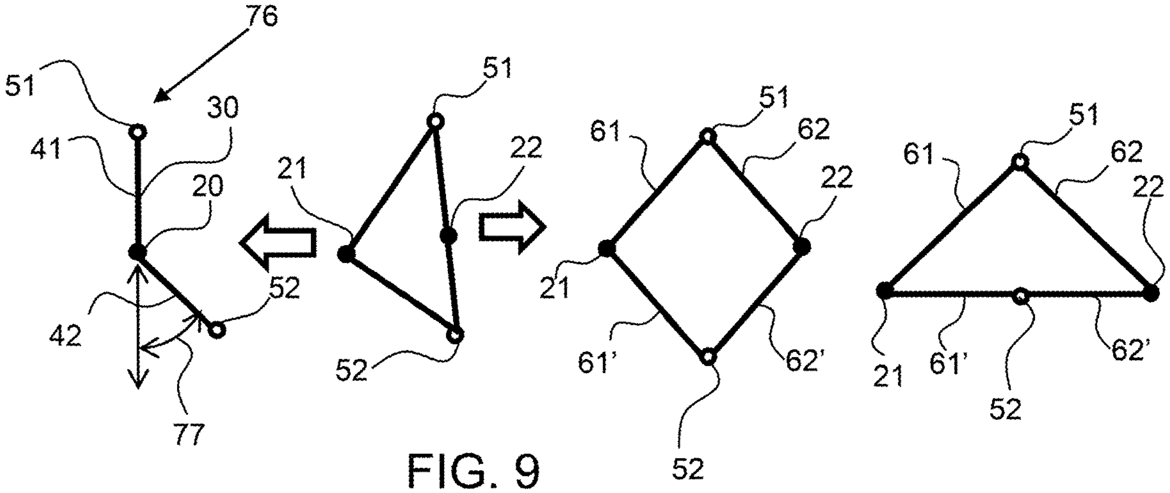

As shown in FIG. 9, a skewed elongated aperture 76 comprises a first extension 41 from a pair of nodes 20 and a second extension 42 from the pair of nodes that extends at an offset angle 77 from alignment with the first extension, whereby they first and second extensions are not aligned, as is the case with a linear elongated aperture shown in FIG. 1. As this skewed elongated aperture is expanded a triangle is initially formed, and then a rectangular shaped polygon aperture is formed; note that the sides may not be equal length and the angles between the sides may not be 90 degrees as is the case with a rectangle. Further expansion of the aperture results in a triangle.

Figure 10:
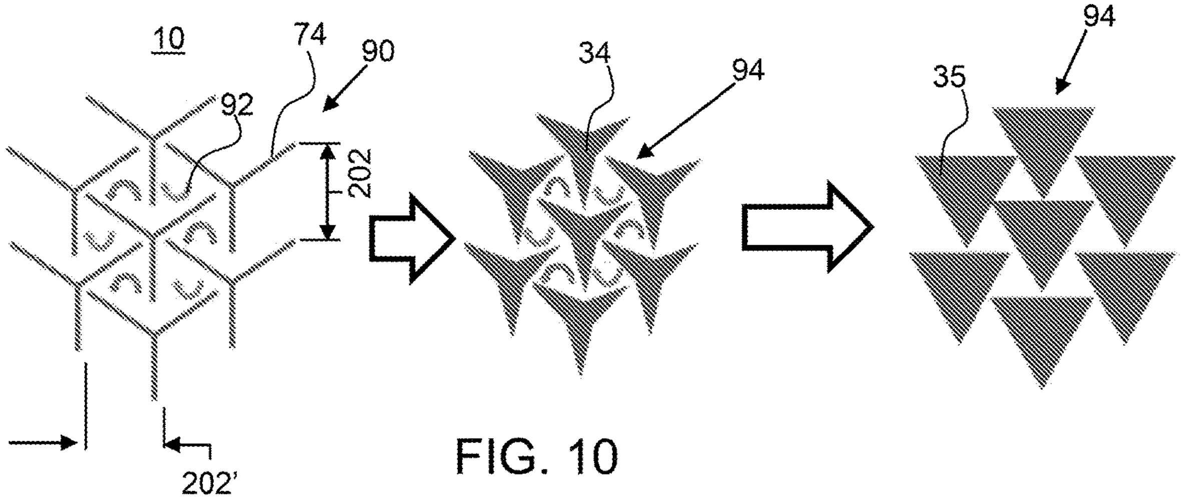
FIG. 10 shows a biological compliant scaffold material having an exemplary geometric pattern of elongated apertures having three antinodes configured at the antinode ends of separate extensions from the pair of nodes and the geometric patterns formed when the graft material is elongated.

As shown in FIG. 10, an exemplary biological compliant scaffold 10 comprises a plurality of Y-shaped apertures 74 configured with the antinodes proximal to a node to produce geometric shapes or tiles 92, therebetween. As the graft is elongated the apertures open up and the tiles therebetween rotate to enable biaxial expansion. The tiles that are connected by a node antinode pair counter rotate and those not connected by a node antinode pair co-rotate. This combination of tile rotation and aperture expansion enables a generally uniform biaxially expansion. As shown the plurality of Y-shaped apertures 74 expand to partially expanded apertures 34 before being further expanded into fully expanded apertures 35. As shown in FIG. 10, the repeat distances 202, 202' are shown in orthogonal directions. These repeat distances are the distances between the same features between adjacent features. The repeat distance in a first direction may be different from a repeat distance in a second or orthogonal direction, as shown. In some cases, the repeat distance in orthogonal directions may be substantially the same, or within about 20% of each other or even within about 10% of each other. As described herein the size of the elongated apertures and/or the repeat distance in one or more directions may change over the surface of a compliant scaffold.

Figure 11:
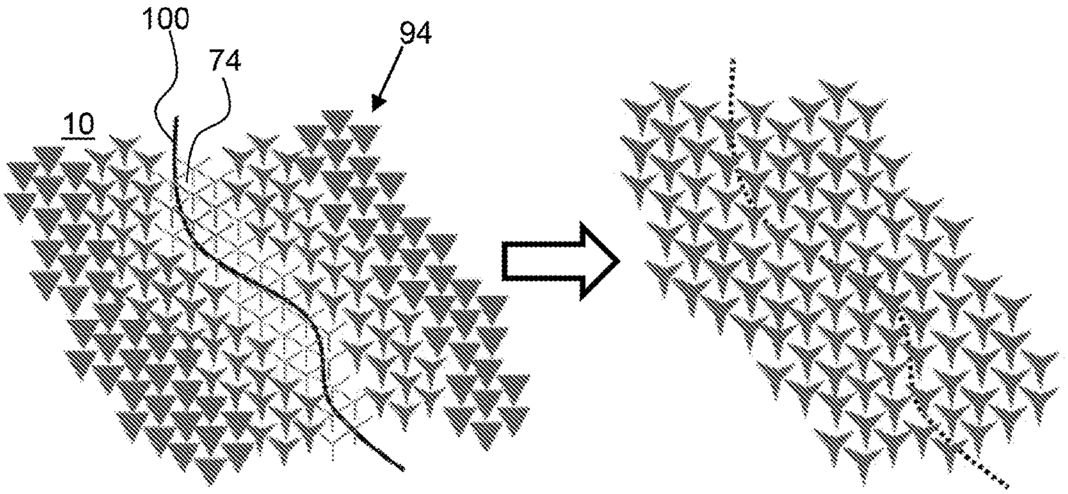
FIG. 11 shows a biological compliant scaffold material having an arrangement of apertures to enable both expansion and contraction around the contours of a wrinkle to diminish the wrinkle.

As shown in FIG. 11, an exemplary in-vivo scaffold comprises a plurality of Y-shaped apertures 74 configured with the antinodes proximal to a node to produce geometric shapes or tiles 92, in tissue, such as skin. This in-vivo scaffold is configured around a wrinkle 100 in the skin. Over time, as indicated by the bold arrow, the apertures that are unexpanded open up, and the fully expanded elongated apertures contract; the tiles rotate to relieve the wrinkles, or indented scars, and diminish the blemish form the surface of the skin. Such a differentially expanded scaffold could be imprinted onto the surface of tissue or skin, with potentially a Laser or specifically designed cutting device that would remove the tissue within the fully expanded areas, essentially pre-programming the scaffold to precisely alter its shape as tissue regenerates. This kind of tissue programming can be performed ex vivo or in vivo on a variety of grafts/flaps/tissues/or biocompatible implants. Such a technique could program blood vessels to shrink, such as varicose veins, or to expand, such as stenotic arteries. FIG. 11 diagrams an exemplary biological compliant scaffold 10 that is differentially expanded as shown on the left side of the bold arrow; wherein some of the elongated apertures or a portion of the plurality of apertures are expanded to a different degree than other elongated apertures. The plurality of elongated apertures proximal to the wrinkle are not expanded, or expanded to a lesser amount than the plurality of elongated apertures configured distal from the wrinkle. The elongated apertures proximal the wrinkle may expand while the expanded scaffold 94, elongated apertures may contract. In this way the scaffold is programmed to selectively alter its own structure or function, including the tissues that the scaffold is directing the regeneration thereof. The central area is programmed to expand while the edges, or outer portions, are programmed to contract. As the scaffold equilibrates, such that the surface reaches a state of homogenous expansion, indicated by the right side of FIG. 11, the edges contract and the center expands. This technique can be used to treat indented wrinkles 100 or scars in skin.

Figure 12:
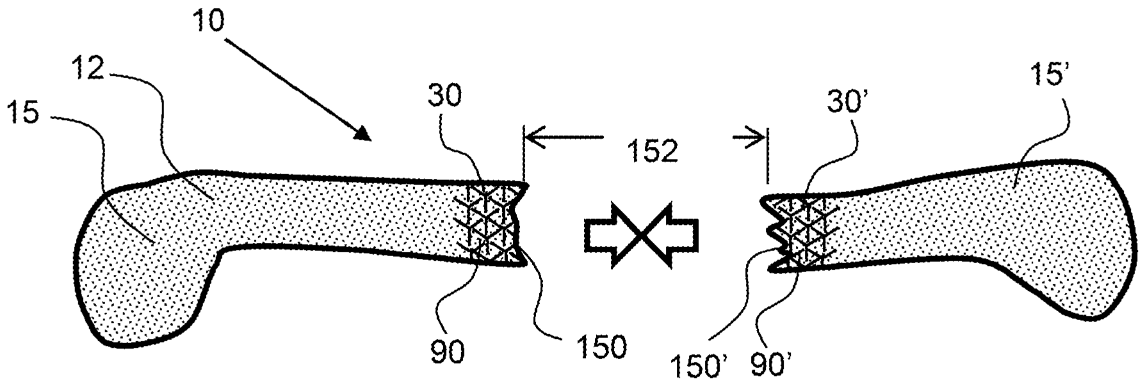
FIGS. 12 to 14 show an exemplary biological compliant scaffold configured in an ex vivo bone that is fractured, wherein a geometric pattern of apertures is formed proximal the first and second fractured ends of the bone to allow expansion of the bone.
Figure 13:
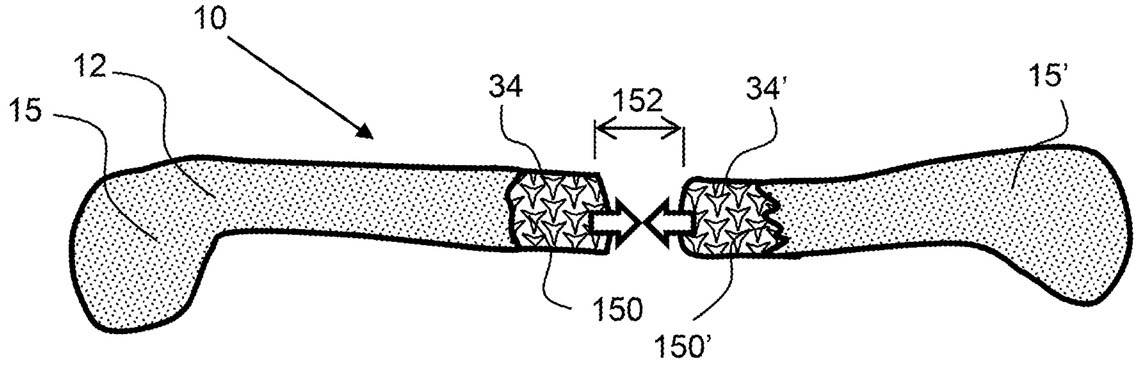
Figure 14:
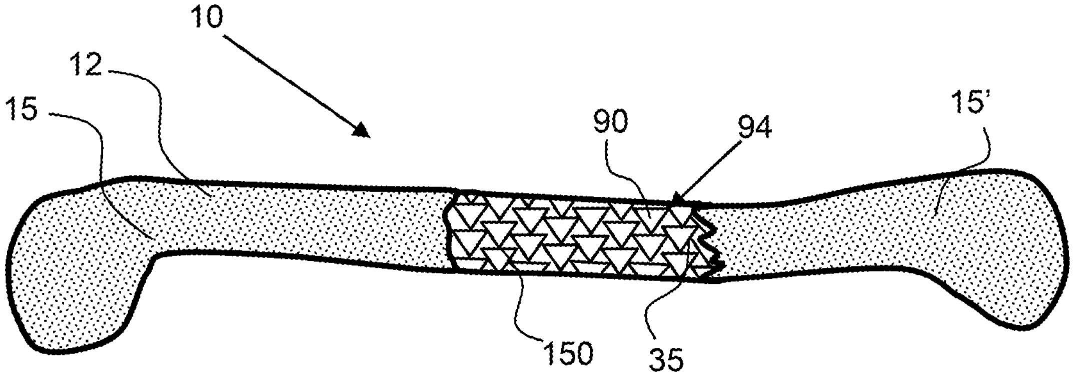

Referring now to FIGS. 12 to 14, an exemplary biological compliant scaffold 10 is configured in an in vivo biological scaffold material 12, bone 15, 15', that is fractured. A geometric pattern of apertures 90, 90' is formed proximal the first fractured end 150 and second fractured end 150' of the bone to allow expansion of the bone. As shown in FIG. 13, the elongated apertures 30, 30' of the geometric pattern of apertures 90, 90', respectively, has expanded to form partially expanded elongated apertures 34, 34' thereby allowing expansion of the bone to reduce the fracture gap 152. As shown in FIG. 14, the elongated apertures are now fully expanded elongated apertures 35 and the fractured bone is now repaired through expansion of the bone facilitated by the geometric pattern of apertures 90 formed therein, which form an expanded scaffold 94 in the bone.

Figure 15:
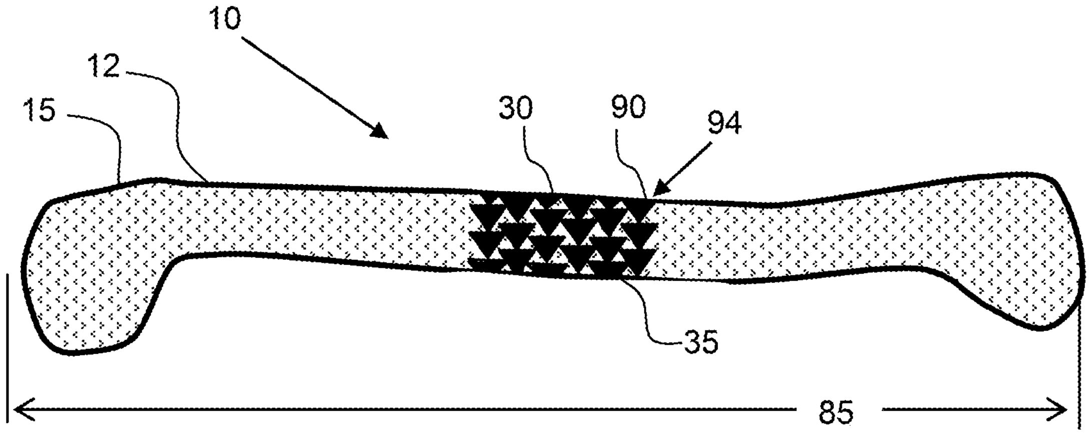
FIGS. 15 to 17 show an exemplary biological compliant scaffold configured in an ex vivo bone for osteoplasty, wherein the bone is shortened by the formation of an expanded scaffold in the bone to cause the bone to shorten.
Figure 16:
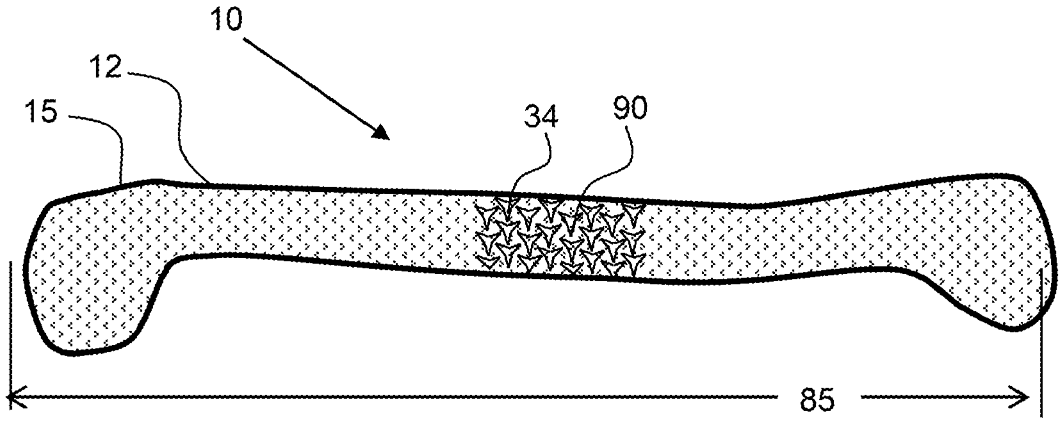
Figure 17:
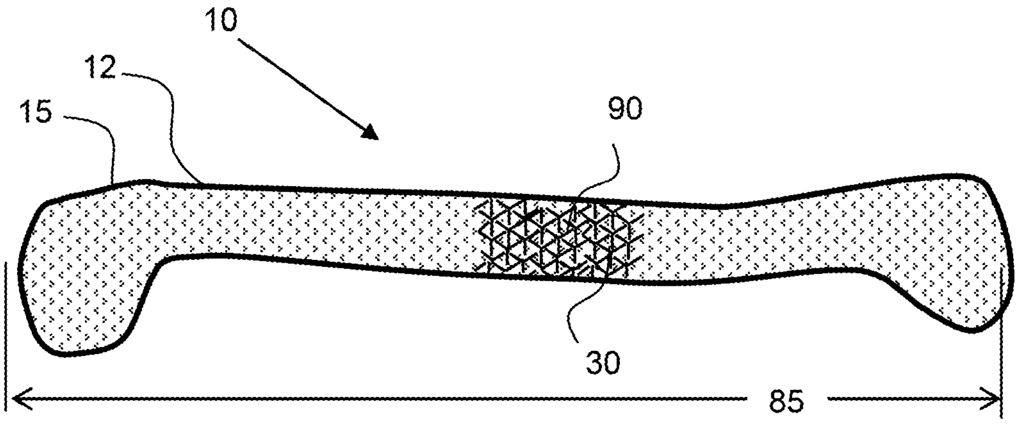

Referring now to FIGS. 15 to 17, an exemplary biological compliant scaffold 10, in this case an expanded scaffold 94, is formed in vivo in a bone 15 to cause the bone to shorten. FIG. 15 shows the pattern of expanded elongated apertures 30 which include expanded apertures 35 formed in the bone and FIG. 16 shows the scaffold reduced in size due to the shortening of the bone and FIG. 17 shows a shortened bone as a result of the formation of a pattern of an expanded scaffold in the bone. The length of the bone 85 is reduced from FIG. 15 to FIG. 17.

Figure 18:
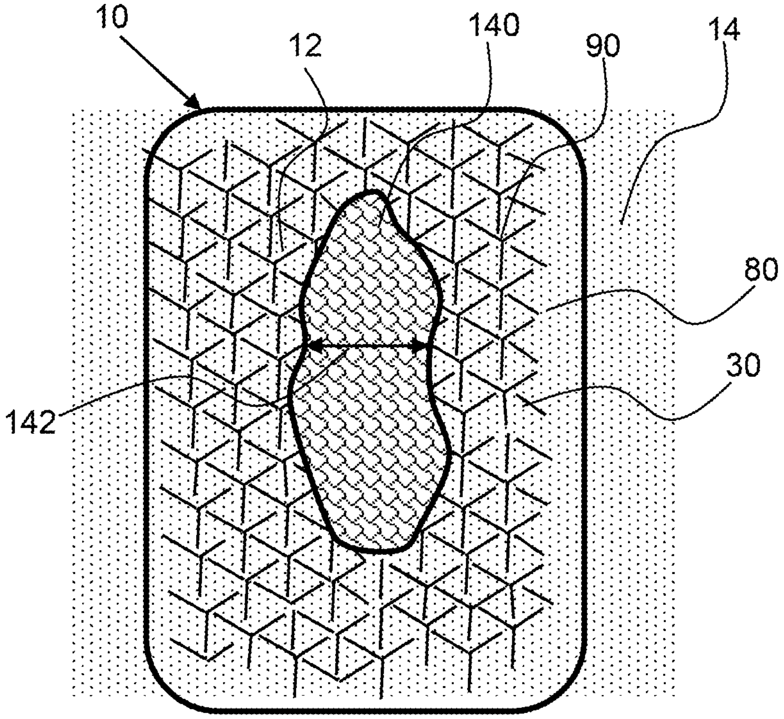
FIGS. 18 and 19 show an exemplary biological compliant scaffold configured in ex vivo tissue, wherein a geometric pattern of apertures is formed around the wound to allow the wound to close with reduced scarring.
Figure 19:
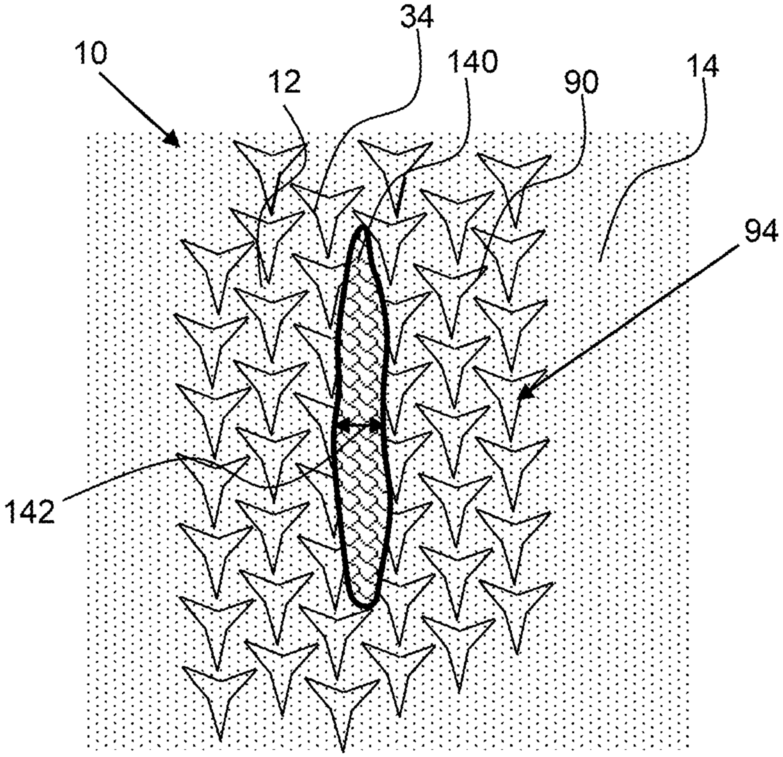

Referring now to FIGS. 18 and 19, an exemplary biological compliant scaffold 10 is configured in an in vivo biological scaffold material 12, tissue 14. A cutting template 80 is configured over a wound in tissue to provide the geometric pattern of apertures 90 for cutting in said tissue. A medical professional may cut the pattern in the tissue around the wound 140 to allow for expansion of the tissue to close the wound and reduce scaring. A geometric pattern of apertures 90 is formed in the tissue around the wound 140 to allow the wound to close with reduced scarring. The plurality of elongated apertures 30 formed are non-expanded apertures as shown in FIG. 18. As shown in FIG. 19, the cutting template is removed and over time, the geometric pattern of apertures 90 expands forming partially expanded elongated apertures 34 to allow the tissue to expand and thereby enable wound closure by the expanded scaffold 94. The wound opening gap distance 142 is reduced from FIG. 18 to FIG. 19 as shown.

Figure 20:
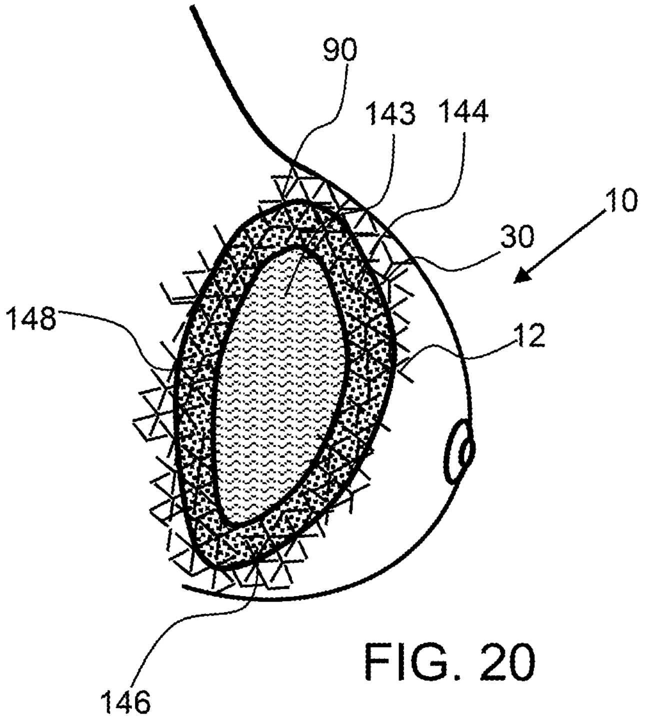
FIGS. 20 and 21 show an exemplary biological compliant scaffold configured in ex vivo breast tissue, wherein a geometric pattern of apertures is formed around a breast implant to reduce or eliminate a stiff capsule formed around the breast implant.
Figure 21:
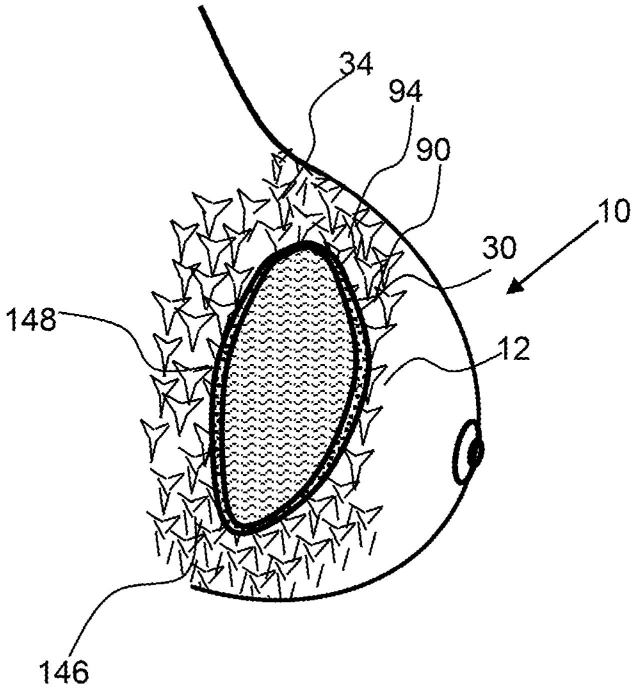
Figure 22:
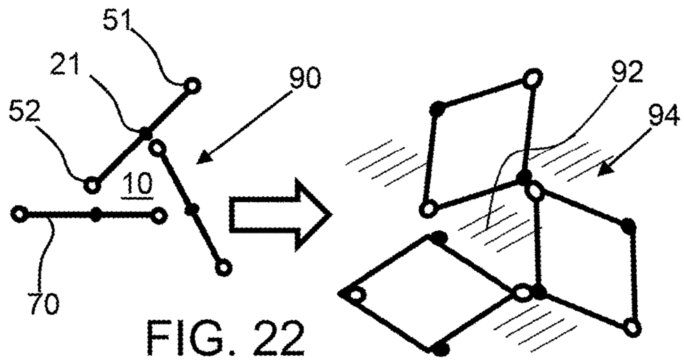
FIGS. 22 to 29 show geometric patterns of apertures in biological compliant scaffold.
Figure 23:
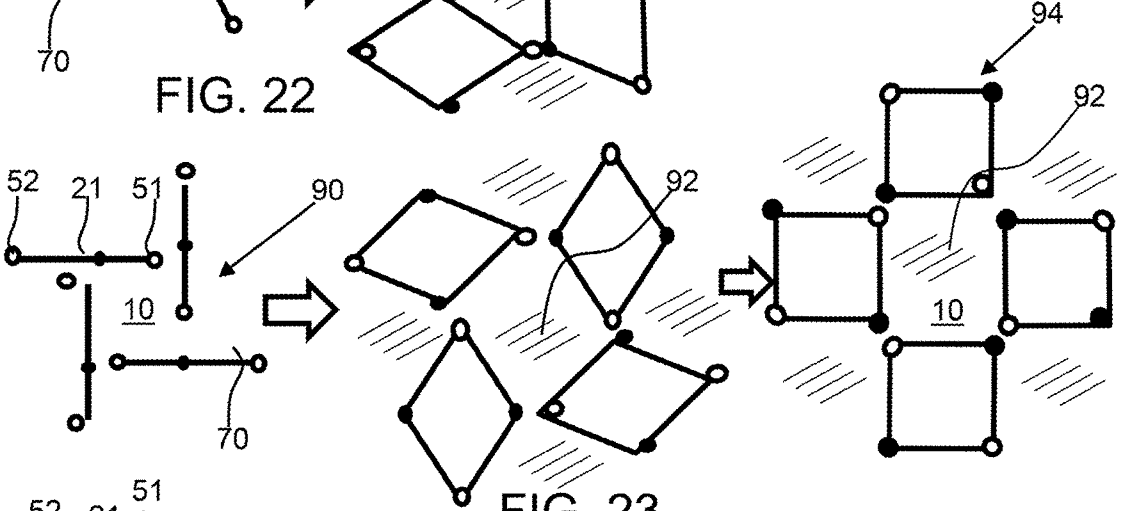
Figure 24:
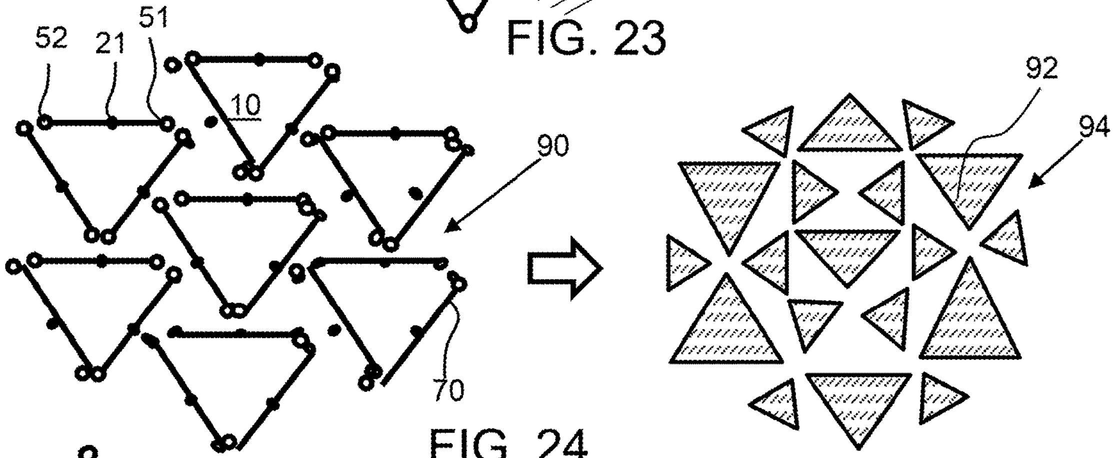

Referring now to FIGS. 20 and 21, an exemplary biological compliant scaffold 10 is configured in in-situ graft material or in-vivo capsules or material already engrafted previously and modified in vivo biological scaffold material 12, breast tissue 146. A geometric pattern of apertures 90 is formed in the stiff capsule 144 of tissue formed around a breast implant 143. The geometric pattern of apertures 90 breaks up the stiff capsule and allows the tissue to reconfigure as shown in FIG. 21, wherein the geometric pattern of apertures 90 is expanded to form expanded elongated apertures 35 or an expanded scaffold 94. This may be performed on tissue around the graft or capsule of on the graft or capsule itself. In addition, grafts may be modified in-situ before they are placed in the breast, around a breast implant or within or upon an already formed breast capsule. The geometric pattern of apertures may have variations in the length of the apertures, inter-aperture distance, or distance between the apertures, and/or changes in gap distance or distance between node and proximal antinode. The geometric pattern may have apertures configured in rows or lines and the distance between adjacent rows may vary over the breast implant or in the breast tissue. This may non-uniform pattern of apertures may be selected and design to enable and promote more conformance and expansion in some desired area and less expansion or conformance in other areas.

Figure 25:
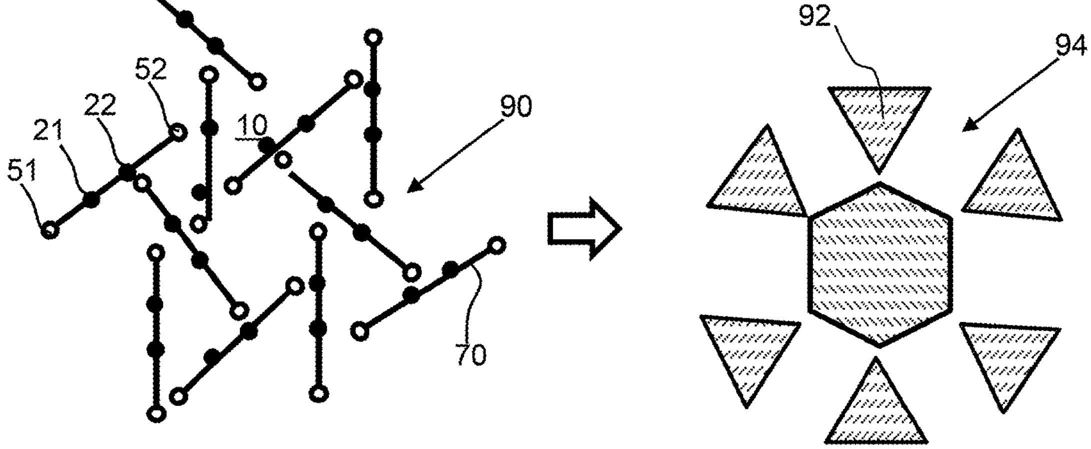

FIGS. 22 to 29 show geometric patterns of apertures 90 in biological compliant scaffold 10. The nodes are indicated by solid small circles while the antinodes are indicated by small open circles. FIGS. 22 to 25 show a geometric pattern of apertures 90 that are an arrangement of I-shaped apertures 70 to form a biological compliant scaffold 10 and the expanded biological compliant scaffold 94. The tiles 92 between the elongated apertures are shown after expansion, as indicated by the bold arrow. FIG. 25 shows a geometric pattern of I-shaped apertures 70 having a first node 21 and a second node 22 between a first antinode 51 and second antinode 52.

Figure 26:
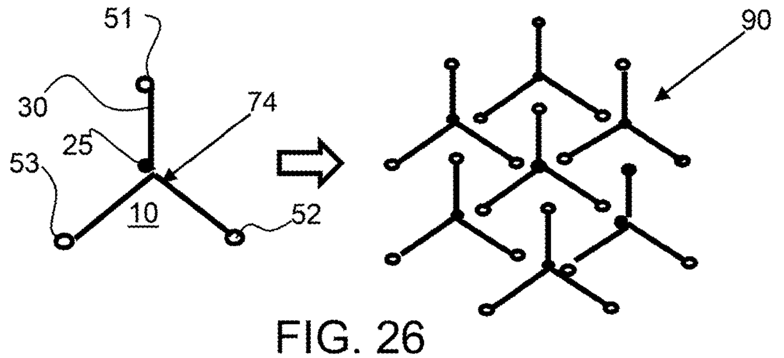

FIG. 26 shows a geometric pattern of Y-shaped apertures 74 in compliant scaffold 10 and configured in a geometric pattern of apertures 90 with antinodes from a first Y-shaped aperture being proximal to and node of a second Y-shaped aperture. Note that the extensions from the proximally located nodes and antinodes may be substantially in alignment, such as within about 20 degrees of each other and preferably within about 10 degrees of each other.

Figure 27:
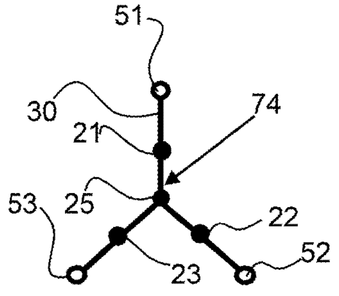

FIG. 27 shows a Y-shaped aperture 74 having an antinode 51, 52 and 53 at the extended end of the extensions of the elongated apertures 30 and nodes 21, 22 and 23 between the intersection of three legs of the Y-shaped aperture and a tri-node 25, at the intersection of the extensions from the antinodes. The nodes 21, 22, 23, along the three legs, or leg nodes, are configured for expansion into separate nodes, as described for FIG. 1.

Figure 28:
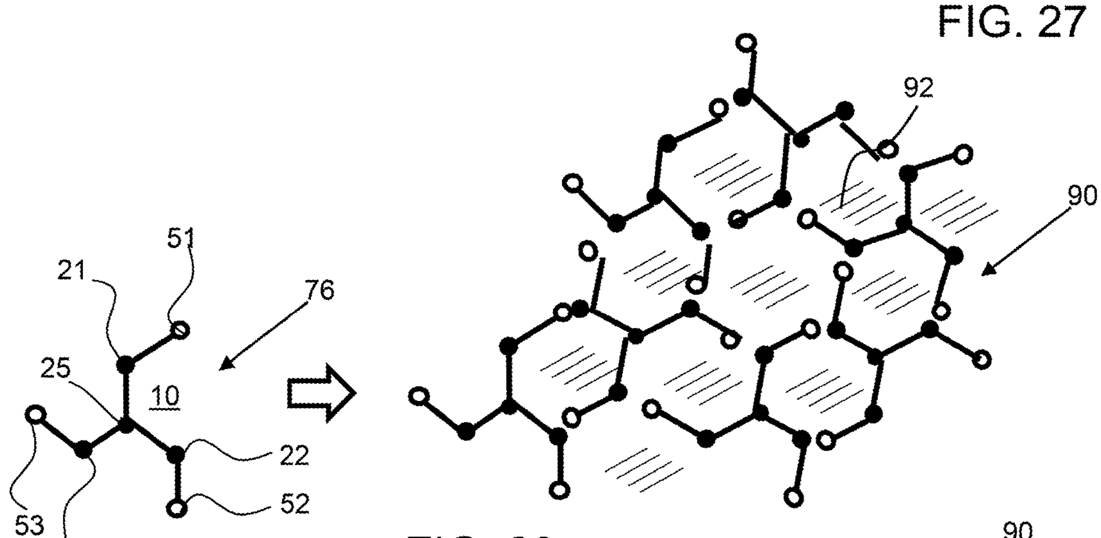

FIG. 28 shows a geometric pattern of apertures 90 that includes skewed shaped apertures 76 and the tiles 92 configured therebetween.

Figure 29:
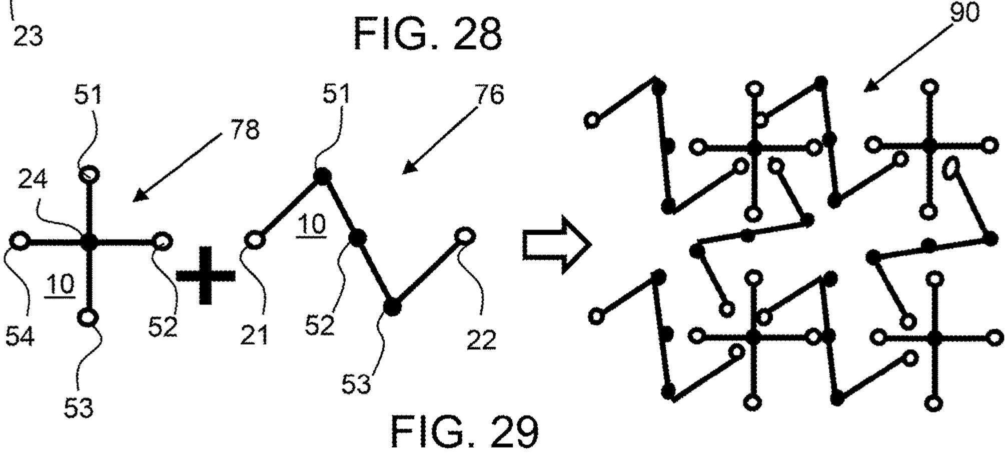

FIG. 29 shows a geometric pattern of apertures 90 including cross-shaped apertures 78 between skewed shaped apertures 76.

Figure 30:
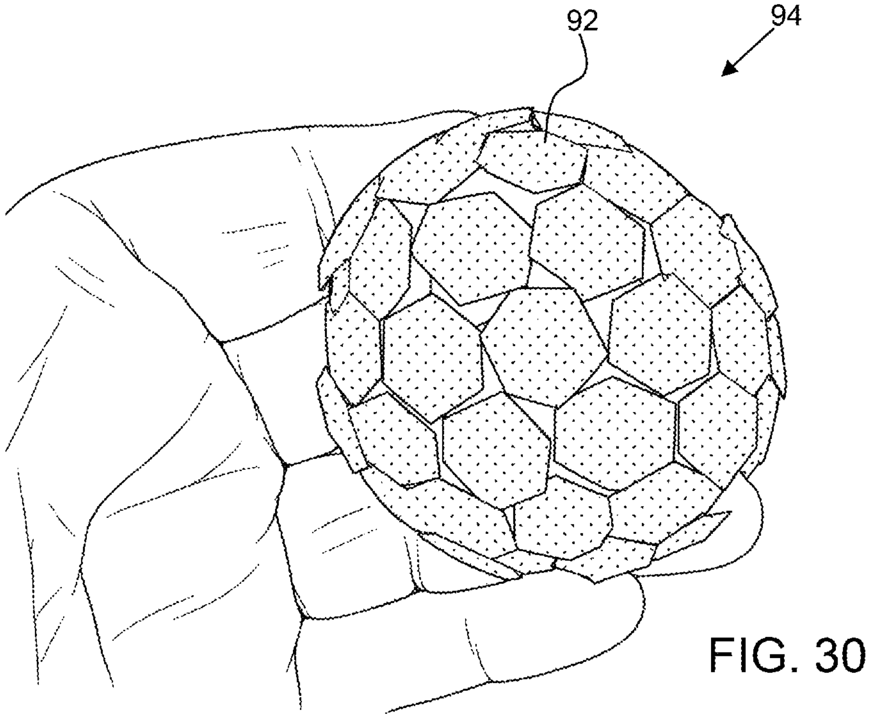
FIG. 30 shows an exemplary biological compliant scaffold material configured around a sphere.
Figure 31:
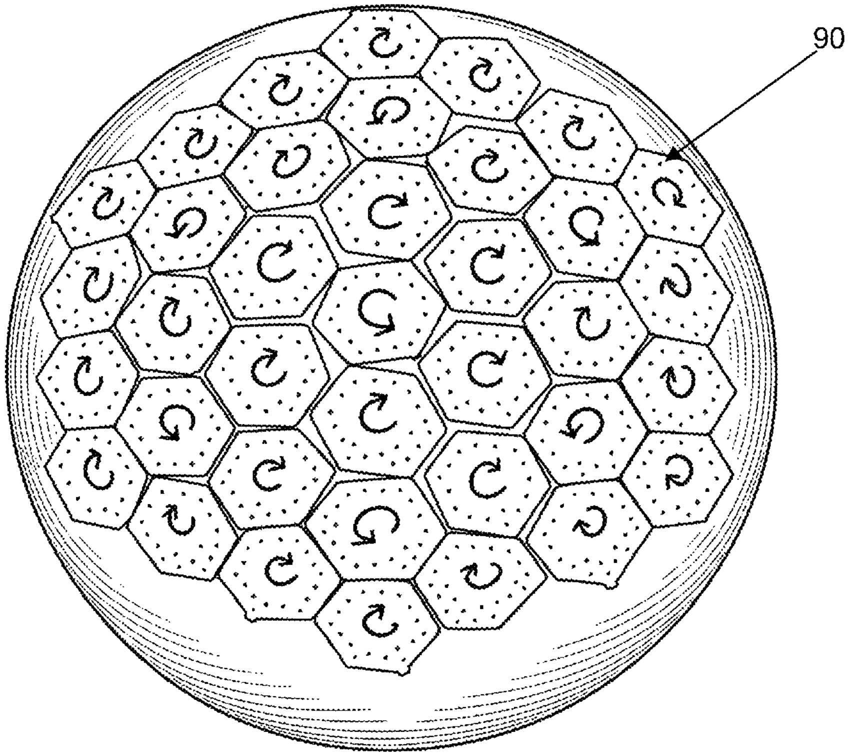
FIG. 31 shows the rotational direction of the spherical biological compliant scaffold material with some tiles co-rotating and some counter rotating.

As shown in FIG. 30, and exemplary biological compliant scaffold 10 can comprise a plurality of apertures configured with the antinodes proximal to a node to produce geometric shapes or tiles 92. The biological compliant scaffold is expanded and forms a compliant spherical shape. FIG. 31 show the rotational direction of the spherical biological compliant scaffold material with some tiles co-rotating and some counter rotating.

Figure 32:
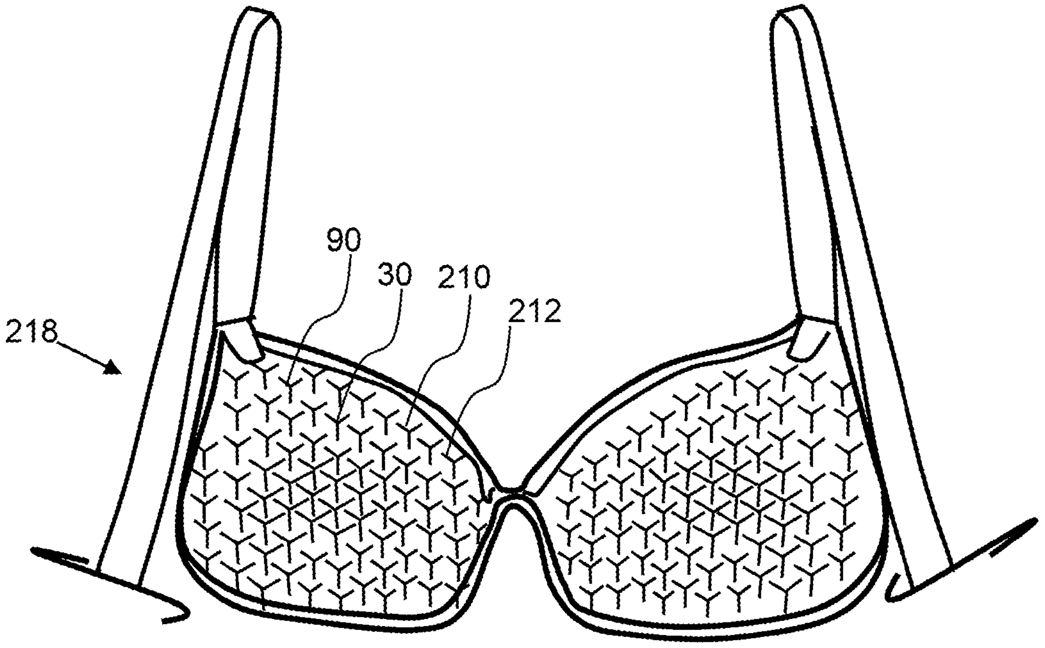
FIG. 32 shows an exemplary brassiere having an apparel compliant scaffold configured as a support cup with a geometric pattern of apertures that is non-uniform.

As shown in FIG. 32 and exemplary brassiere 218, an article of apparel has an apparel compliant scaffold 210 configured as a support cup 212 with a geometric pattern of apertures 90. The pattern of a geometric pattern of apertures is non-uniform with a higher density in the center of the brassiere to promote elongation of the support forward versus down. The length of the apertures may be greater proximal the center, the inter-aperture distance may be smaller and/or the gap distance between node and antinodes may be smaller proximal the center. The size and the gap distance and/or repeat distance may vary over the support cup as shown or an any other suitable pattern for comfort and for appearance attributes.

Figure 33:
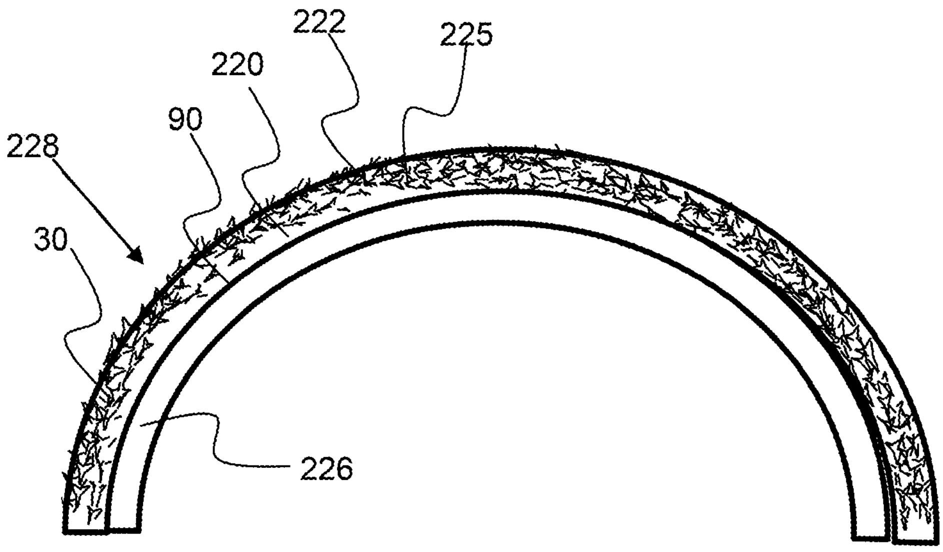
FIG. 33 shows an exemplary structural article that has a structural compliant scaffold configured as a support layer with a geometric pattern of apertures 90.

As shown in FIG. 33 and exemplary structure 228 has a structural compliant scaffold 220 configured as a support layer 222 with a geometric pattern of apertures 90. The pattern of a geometric pattern of apertures may be non-uniform with a higher density in areas of higher expansion. An expandable structure 226 is expanded into a dome shape to cause the structural compliant scaffold 220 to expand and conform to the dome shape. A structural material 225, such as cement, is coated onto the structural compliant scaffold and allowed to set before the expandable structure is unexpanded and removed, leaving a domed structure.

Figure 34:
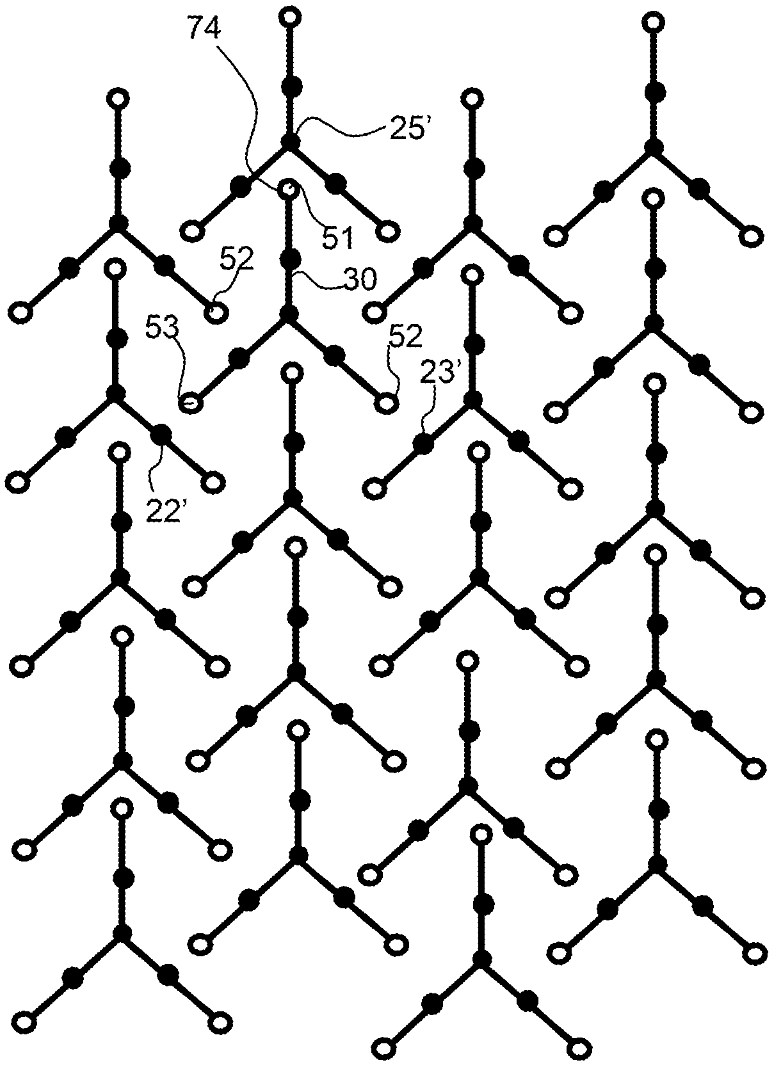
FIG. 34 shows an exemplary geometric pattern of Y-shaped apertures, as shown in FIG. 27, arranged with the first antinode of a first elongated aperture proximal to the tri-node of a first adjacent elongated aperture and the second antinode and third antinode of the first elongated aperture configured proximal to the third node and second node of a second and third adjacent elongated aperture, respectively.

FIG. 34 shows an exemplary geometric pattern of Y-shaped apertures 74, as shown in FIG. 27, arranged with the first antinode 51 of a first elongated aperture proximal to the tri-node 25 of a first adjacent elongated aperture and with the second antinode 52 of the first elongated aperture configured proximal to a third node 23' of a second adjacent elongated aperture, and the third antinode 53 of the first elongated aperture configured proximal to a second node 22' of a third adjacent elongated aperture.

Figure 35:
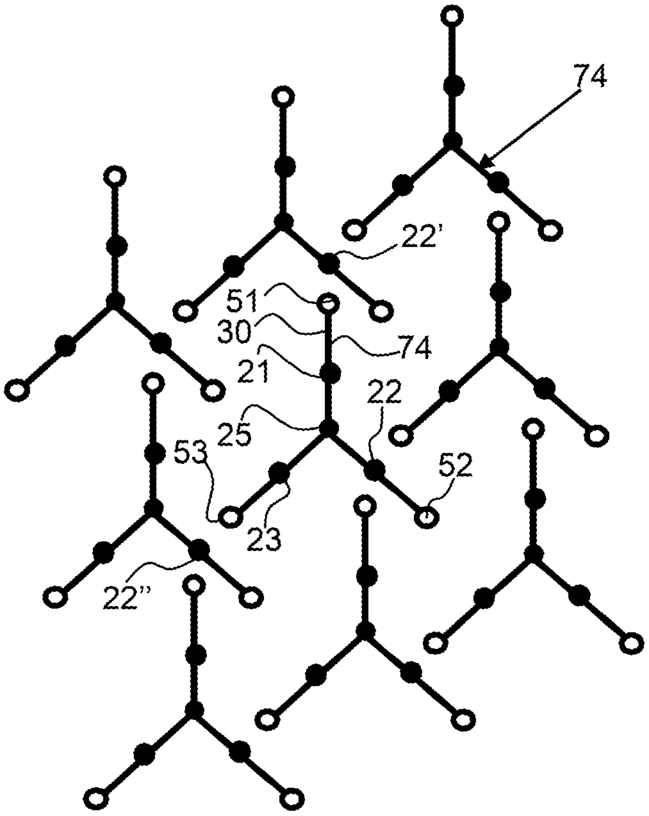
FIG. 35 shows an exemplary geometric pattern of Y-shaped apertures, as shown in FIG. 27, arranged with the first antinode of a first elongated aperture proximal to the second node of a first adjacent elongated aperture and the third antinode of the first elongated aperture configured proximal to the second node of a second adjacent elongated aperture.

FIG. 35 shows an exemplary geometric pattern of Y-shaped apertures 74, as shown in FIG. 27, arranged with the first antinode 51 of a first elongated aperture proximal to the second node 22' of a first adjacent elongated aperture and with the third antinode 53 of the first elongated aperture configured proximal to the second node 22'' of a second adjacent elongated aperture. The second node 22 of the first elongated aperture is proximal to the antinodes of two other elongated apertures.

Figure 36:
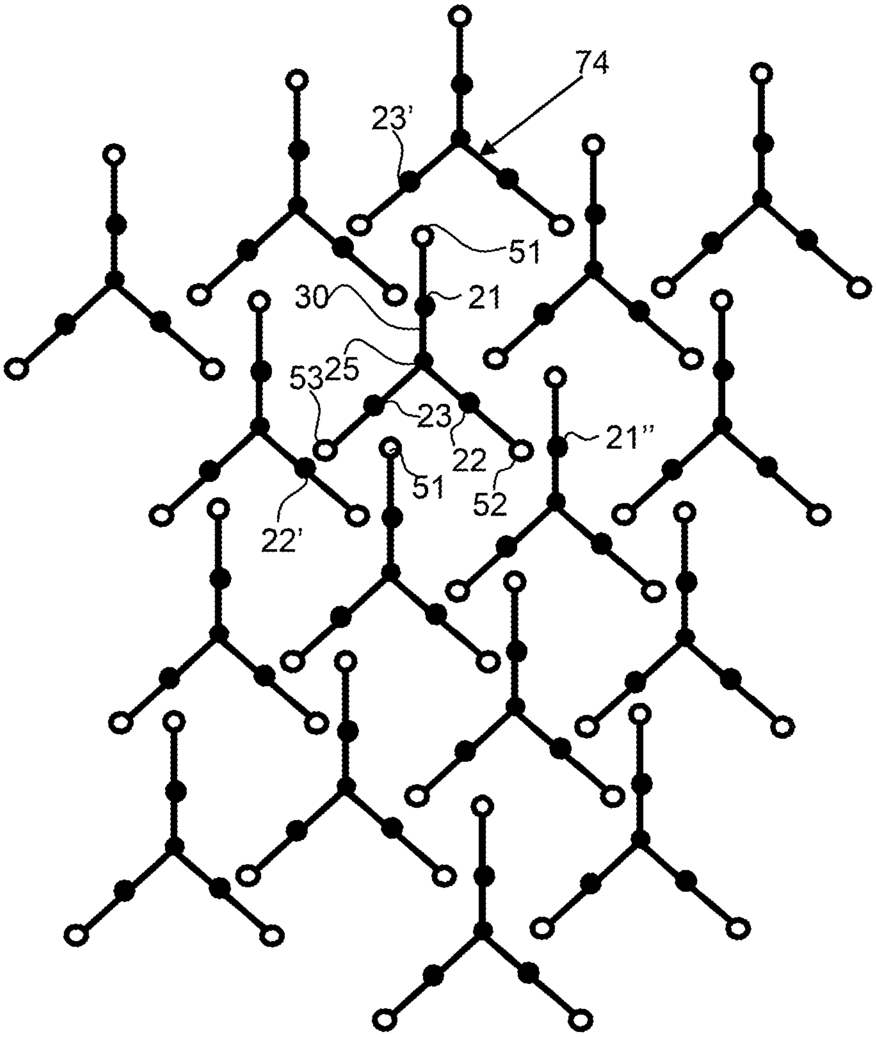
FIG. 36 shows an exemplary geometric pattern of Y-shaped apertures, as shown in FIG. 27, arranged with the first antinode of a first elongated aperture proximal to the third node of a first adjacent elongated aperture and the second antinode of the first elongated aperture configured proximal to the first node of a second adjacent elongated aperture and the third antinode of the first elongated aperture configured proximal to the second node of a third adjacent elongated aperture such that each node of the first elongated aperture is proximal to a different arm antinode of three different adjacent elongated apertures.

FIG. 36 shows an exemplary geometric pattern of Y-shaped apertures 74, as shown in FIG. 27, arranged with the first antinode 51 of a first elongated aperture proximal to the third node 23' of a first adjacent elongated aperture, the second node 52 of the first elongated aperture configured proximal to a first node 21' of a second adjacent elongated aperture and with the third antinode 53 of the first elongated aperture configured proximal to the second node 22' of a third adjacent elongated aperture such that each node of the first elongated aperture is proximal to a different arm antinode of three different adjacent elongated apertures.

The properties of the compliant scaffold can be altered by changing the orientation of the elongated apertures to modify the node/adjacent antinode configurations. As shown in FIG. 34, the antinode of one elongated aperture is configured proximal to a tri-node. In FIG. 35, the same antinode is now slid along the leg of the adjacent elongated aperture to be proximal to the second antinode, or an antinode configured between the tri-node and the node configured on the extended end of the leg. Note that the antinode may be moved and positioned along any portion of the leg extension from the tri-node. This is the case in FIG. 27. Moving the point of interaction of nodes to adjacent antinodes decreases the expansion ratio of the Y-shaped or triradiate elongated aperture from approximately 2.3 to 1 to almost 1 to 1 when the node antinode pairs approach the terminus of the extension. FIGS. 34 to 36 show variations in relative positionings of the triradiate apertures relative to each other. These adjustments allow for fine tuning the stiffness and expansile properties of the mesh for a specific application. Cutting devices could be configured to mesh any pattern into a conformable mesh by simply adjusting the spacing between elongated apertures and/or adjusting relative position of adjacent apertures with respect of distance from the center.

Figure 37:
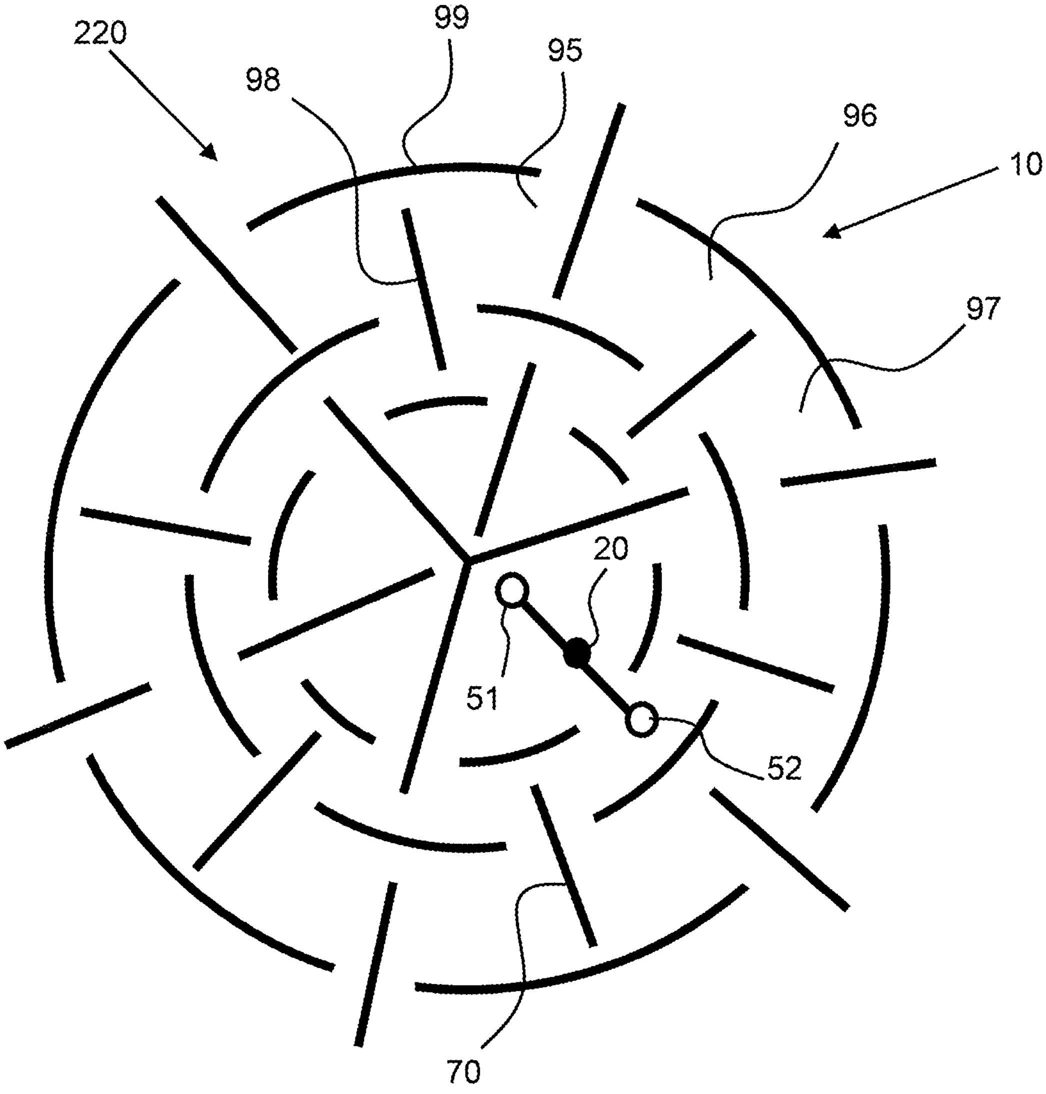
FIG. 37 shows an exemplary compliant scaffold with a non-uniform geometric pattern of apertures that is configured in a circular array, with some of the apertures extending radially, radial apertures and other apertures extending circumferentially, or circumferential apertures.
Figure 38:
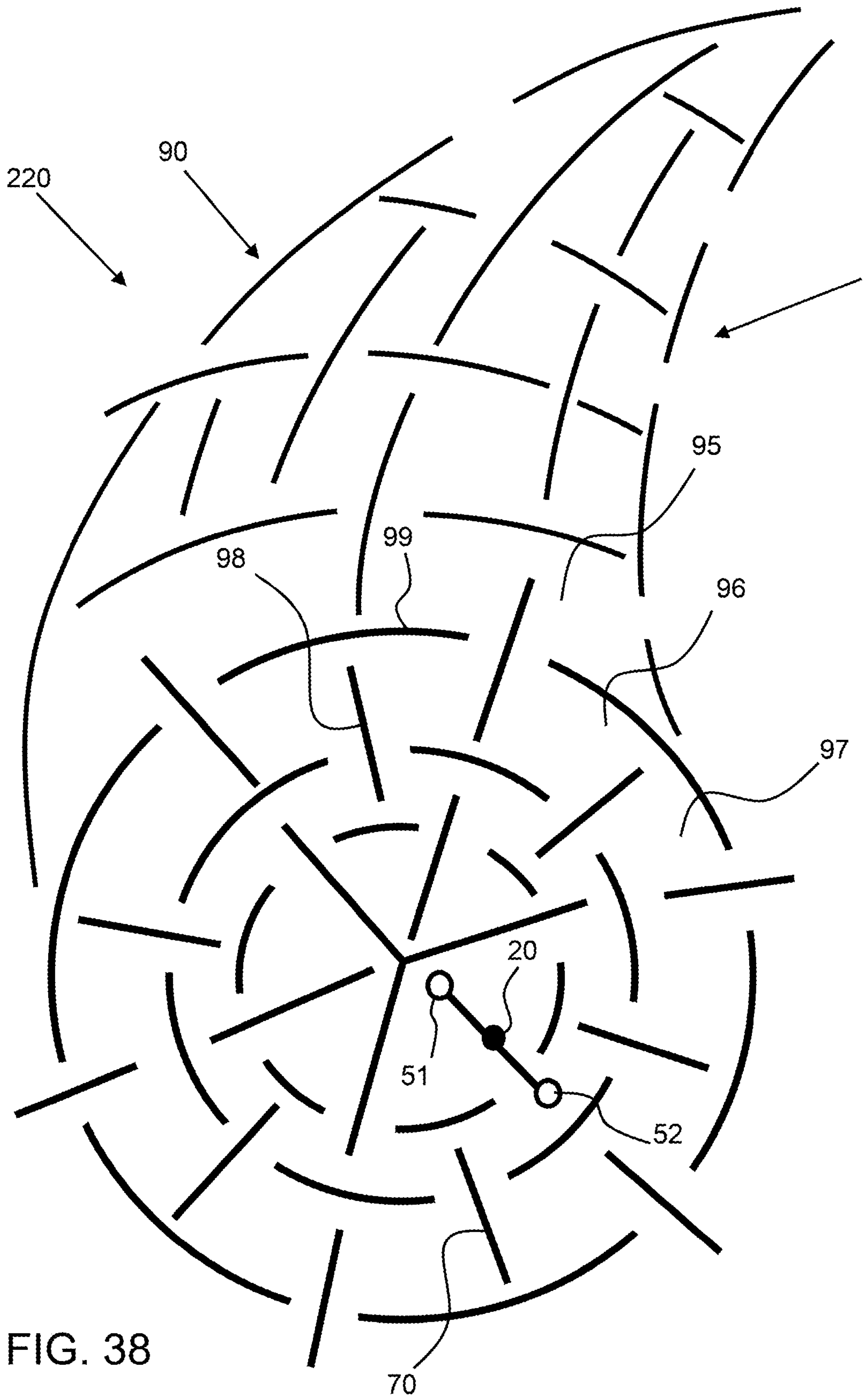
FIG. 38 shows an exemplary compliant scaffold with a non-uniform geometric pattern of apertures that is configured in a circular pattern of apertures with some of the apertures extending radially, radial apertures and other apertures extending circumferentially, or circumferential apertures, and an additional geometric pattern of apertures extending from the circular array.

Referring now to FIGS. 37 and 38, an exemplary compliant scaffold 220 is configured with a control geometric pattern of apertures 95 comprising a non-uniform geometric pattern of apertures 96 that is configured in a circular pattern of apertures 97, with some of the apertures extending radially, radial apertures 98, and other apertures extending circumferentially, circumferential apertures 99. The circumferential apertures are progressively longer as they progress outward in a concentric pattern about a center of the circular pattern of apertures. This circular pattern of apertures 97 may allow for a spherical deformation of the compliant scaffold to produce a round or smoothly curved compliant scaffold. This may be used in cosmetic implantation applications, such as for breast augmentation, wherein the circular pattern of apertures is configured in the breast implant, a cover for the breast implant and/or in tissue or an implant configured to the tissue around the breast implant. The circular pattern of apertures 97 includes I-shaped apertures 70 having a node configured between a first antinode 51 and second antinode 52, configured on the ends of the aperture.

As shown in FIG. 38, an exemplary compliant scaffold 220 is configured with an additional geometric pattern of apertures extending from the circular pattern of apertures 97.

Figure 39:
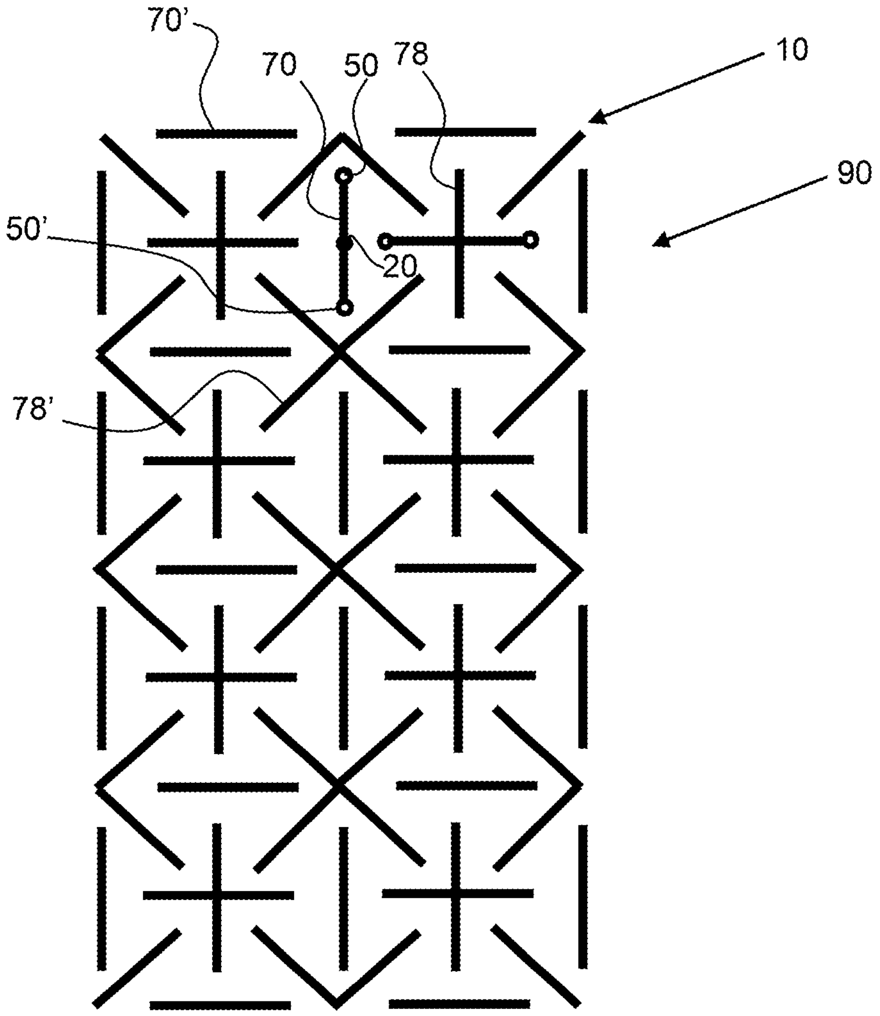
FIG. 39 shows an exemplary geometric pattern of apertures that includes a plurality of columns of cross-shaped apertures configured in spaced apart columns and a plurality of angularly offset cross-shaped apertures, angularly offset or turned 45 degrees with respect to the cross-shaped apertures in the pair of columns and configured between the columns of cross-shaped apertures.

As shown in FIG. 39, an exemplary geometric pattern of apertures 90 includes a plurality of columns of cross-shaped apertures 78 configured in spaced apart columns and a plurality of angularly offset cross-shaped apertures 78', angularly offset or turned 45 degrees with respect to the cross-shaped apertures in the pair of columns and configured between the columns of cross-shaped apertures. The angularly offset cross-shaped apertures may be angularly offset substantially 45 degrees from the cross-shaped apertures in the pair of columns, or from about 30 degrees offset to about 60 degrees offset. As shown the angularly offset cross-shaped apertures 78' are 45 degrees offset. Also, around each of the cross-shaped apertures configured in spaced apart columns, I-shaped apertures 70 are configured to form a perimeter around each of these cross-shaped apertures 78. These I-shaped apertures have antinodes 50, 50' that are proximal the intersection of the cross-shaped apertures 78'. The I-shaped apertures are shown in more detail in FIG. 4 and the cross-shaped apertures are show in more detail in FIG. 7. This particular geometric pattern of apertures enables expansion to conform to a spherical or curved surface.

Figure 40:
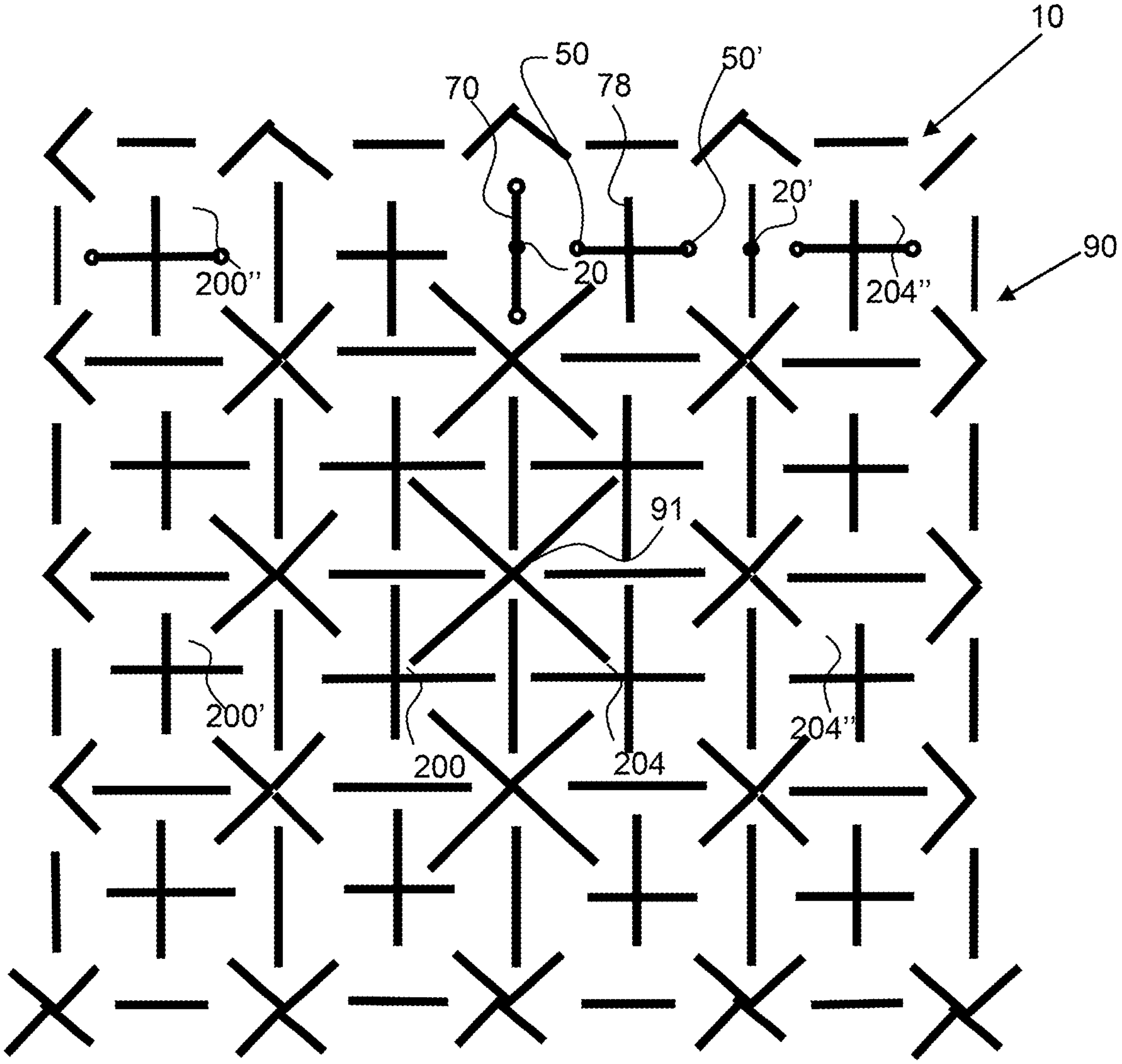
FIG. 40 shows the exemplary geometric pattern of apertures shown in FIG. 39, modified to produce a dome shape around the middle of the geometric pattern of apertures or mesh, wherein the spacing between the apertures is not changed, but rather the distance between the node-antinode pairs is changed to produce a preferential and pre-programmed compliance and expansion into a down shape.

As shown in FIG. 40, the exemplary geometric pattern of apertures 90 shown in FIG. 39 is modified to produce a dome shape around the center 91 of the geometric pattern of apertures, or mesh, wherein the spacing between the apertures is not changed, but rather the gap distance 200 between the node-antinode pairs is changed to produce a preferential compliance that is designed to produce expansion into a dome shape. The geometric pattern further from the center, the center of the largest cross-shaped aperture, has shorter apertures and greater gap distances 200', 200" between node-antinode pairs. As shown, the gap distance 200' is more than double the gap distance 200, proximal the center, and gap distance 200" is more than five times gap distance 200. This gap distance produces a living hinge 204, 204', 204", wherein the apertures can rotate about said living hinges for compliance to a shape. Theses living hinges become larger further away from the center and therefore conformability decreases. This gradient in the gap distances and living hinges, with progressively larger gap distances and progressively longer living hinges with distance from the center of the design, or area with the shortest gap distances and living hinges, constricts expansion proportionately with the distance from the center of the mesh. This is useful for creating domed or hemispherical shapes. This geometric pattern of apertures 90 comprises I-shaped apertures 70 and cross-shaped apertures 78, each having nodes 20, 20' and antinodes 50, 50'.

Figure 41:
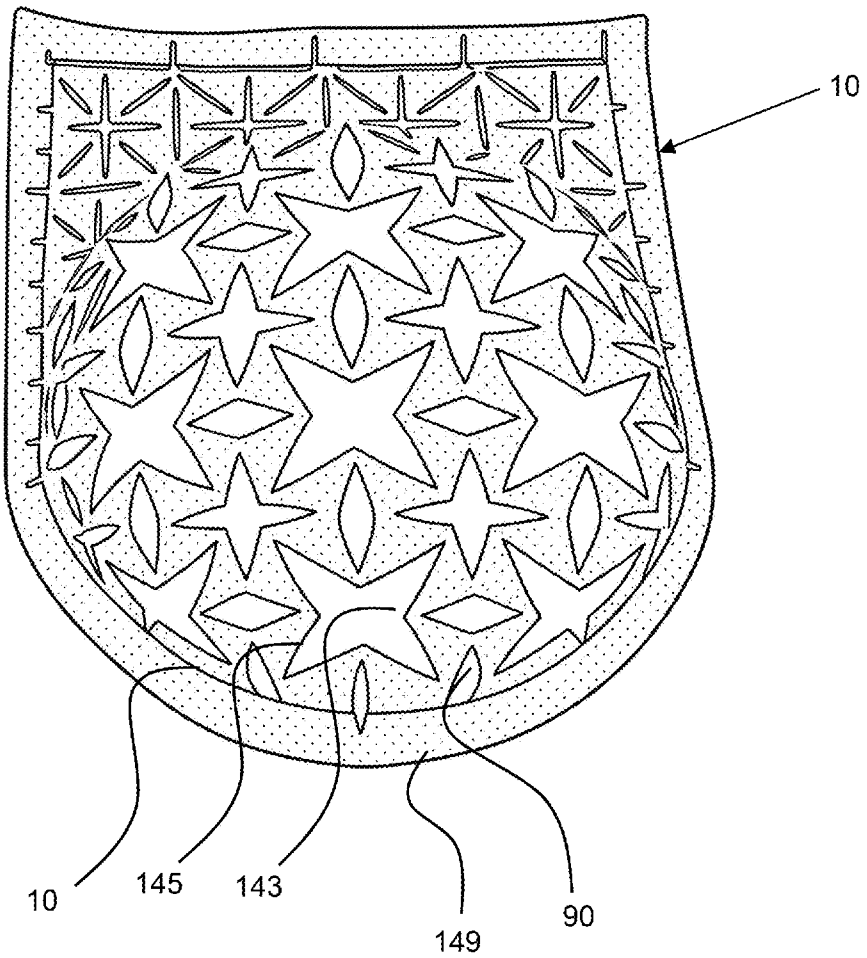
FIG. 41 shows a breast implant configured under a biological compliant scaffold, or graft of material having the geometric pattern of apertures shown in FIG. 39, wherein the breast implant has caused both the offset column of cross shaped apertures and the cross-shaped apertures therebetween to expand to enable conformance around the spherical shape of the breast implant.

As shown in FIG. 41, a breast implant 143 is configured under a biological compliant scaffold 10, or graft of material having the geometric pattern of apertures 90 shown in FIG. 39. The breast implant has caused both the offset column of cross shaped apertures and the cross-shaped apertures therebetween to expand to enable conformance around the spherical shape of the breast implant. The biological compliant scaffold may be a sheet of material that at least partially covers the breast implant and may be coupled to tissue to secure the biological compliant scaffold in a fixed position within the body. The breast implant may then form and hold a more desired shape as it is retained by the biological compliant scaffold 10. The biological compliant scaffold may be a sheet of material as shown, or may form an envelope or pouch and the geometric pattern of apertures may be configured on only one side, the side facing the skin of the patient, to promote the desired shape being formed and retained. A breast implant may be a differentially compliant breast implant 145, having a biological compliant scaffold 10 with a geometric pattern of apertures 90 that is differentially compliant having a designed gradient or change in gap distances or living hinge lengths between apertures or node-antinode pairs. The differentially compliant breast implant 145 has an attachment portion 149, a perimeter flange, that may be used to attach the biological compliant scaffold 10 to tissue.

Figure 42:
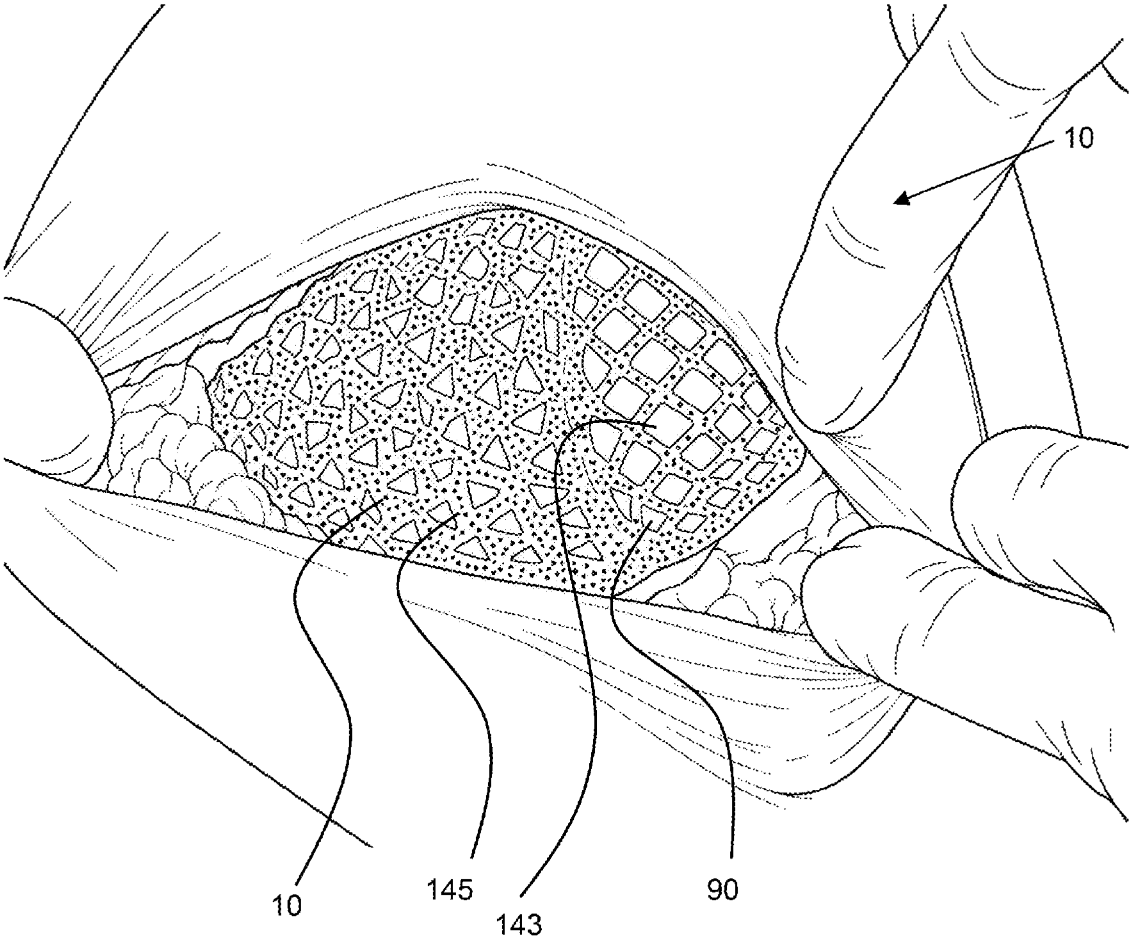
FIG. 42 shows a breast implant that is configured with an exemplary biological compliant scaffold having a predefined geometric pattern of apertures to enable differential compliance or expansion in a preferred and predefined manner to produce a desired shape.

As shown in FIG. 42, a breast implant 143 is configured with an exemplary biological compliant scaffold 10 that has a predefined geometric pattern of apertures 90 to enable differential compliance or expansion in a preferred and pre-defined manner to produce a desired shape. In this case, the space between node-antinode pairs may be changed while the spacing between the pattern or apertures remains constant, as shown in FIG. 40. The differentially compliant breast implant 145 enables formation and retention of a desired shape.

Figure 43:
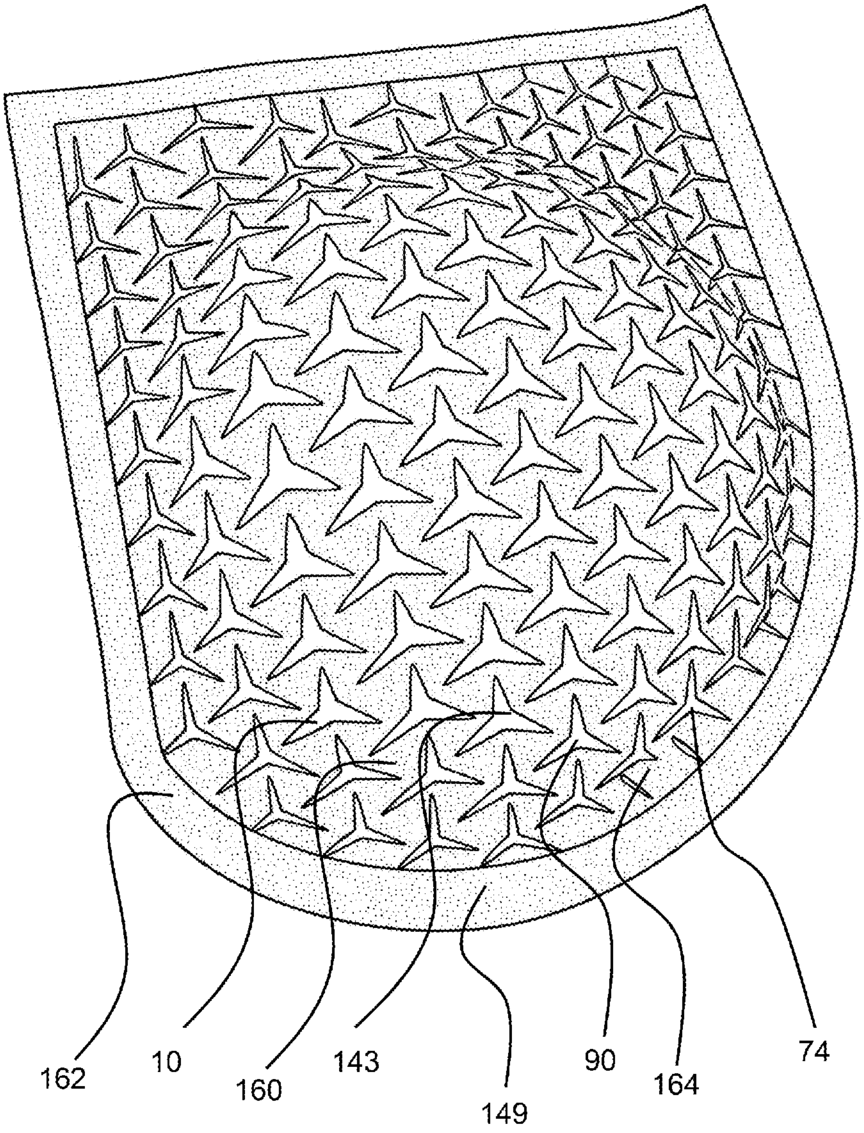
FIG. 43 shows a breast implant breast implant configured within a compliant pouch comprising an exemplary biological compliant scaffold that has a predefined geometric pattern of apertures to enable differential compliance or expansion in a preferred and predefined manner to produce a desired shape.

As shown in FIG. 43, a breast implant 143 is configured within a compliant pouch 160 comprising an exemplary biological compliant scaffold 10 that has a predefined geometric pattern of apertures 90 to enable differential compliance or expansion in a preferred and predefined manner to produce a desired shape. The pattern includes Y-shaped apertures 74 and the spacing between the node-antinode pairs may be changed over the geometric pattern of apertures to produce the differential compliance. The Y-shaped apertures more proximal to the center may comprise longer extensions and thereby shorter gap distances and shorter living hinges between node-antinode pairs. The compliant pouch 160 may be formed into a compliant enclosure 164 by sealing or attaching an opening, for receiving the breast implant, prior to completing the procedure, and may include an attachment portion 149, such as a perimeter edge 162 that is configured for attachment to the tissue to secure the breast implant and pouch in a desired position.

Figure 44:
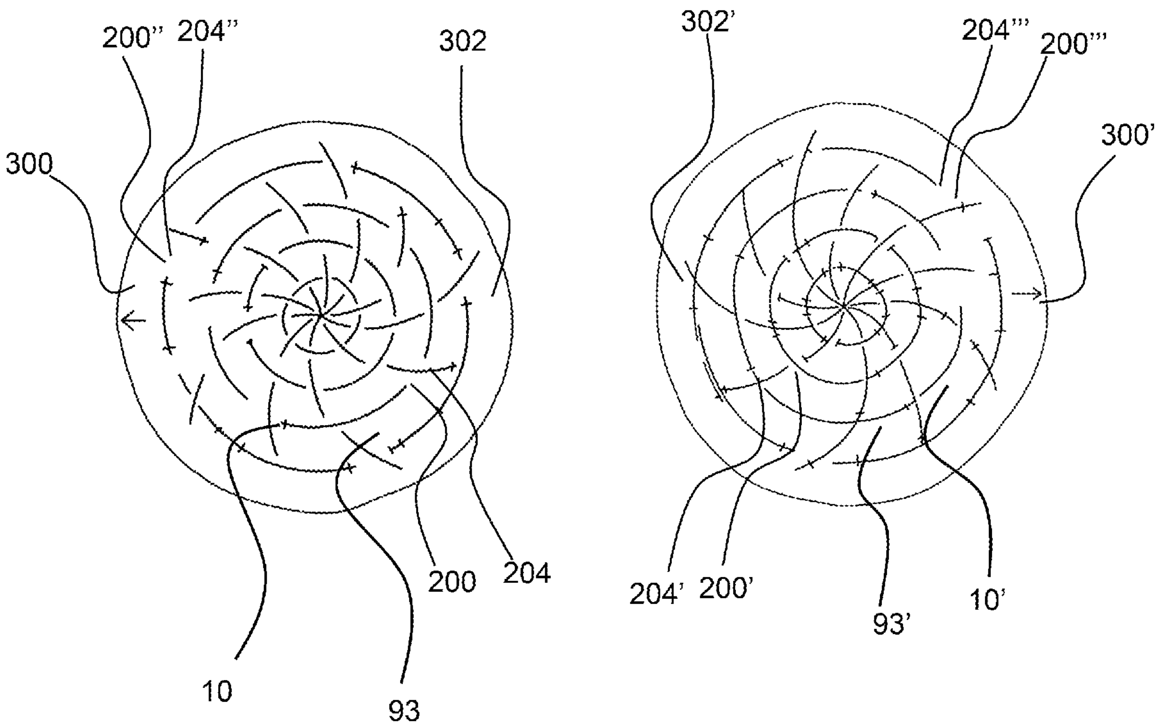
FIG. 44 show a pair of biological compliant scaffolds that are configured for breast augmentation wherein the biological compliant scaffolds are configured to produce a dome shaped breast implant that extends more medially than laterally to produce cleavage.

FIG. 44 show a pair of biological compliant scaffolds 10, 10' that are configured for breast augmentation wherein the biological compliant scaffolds are configured to produce a dome shaped breast implant that extends more medially than laterally to produce cleavage. The biological compliant scaffold 10 is for the right breast and biological compliant scaffold 10' is for the left breast and each comprises a differentially compliant geometric pattern of apertures 93, or as described for FIGS. 37 and 38, a control geometric pattern of apertures 95 comprising a non-uniform geometric pattern of apertures 96 that is configured in a circular pattern of apertures 97, with some of the apertures extending radially, radial apertures 98, and other apertures extending circumferentially, circumferential apertures 99. As shown the biological compliant scaffolds for the right breast and left breast are configured for preferential expansion toward the medial sides 302, 302', or toward the center of the chest than the lateral sides 300, 300'. The gap distances 200, 200' and living hinges 204, 204' on the lateral sides are larger than the gap distances 200", 200'" and living hinges 204", 204'" on the medial sides. The biological compliant scaffolds may be a sheet of biological material, a pouch or an enclosure for the breast implant.

Figure 45:
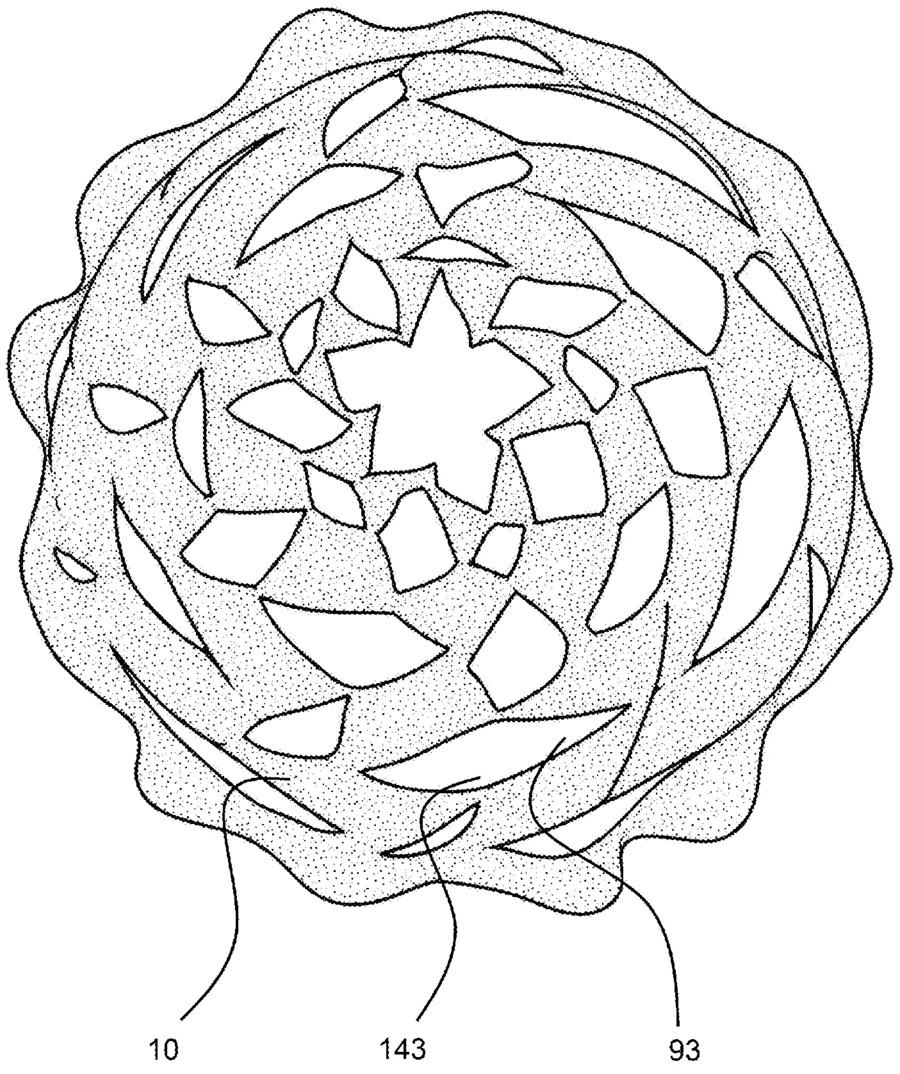
FIG. 45 shows an exemplary biological compliant scaffold that is configured over a breast implant and has differentially compliant geometric pattern of apertures configured for expansion toward a medial side.

As shown in FIG. 45, an exemplary biological compliant scaffold 10 is configured over a breast implant 143 and has a differentially compliant geometric pattern of apertures 93. This biological compliant scaffold 10 may be configured for expansion toward a medial side.

Figure 46:
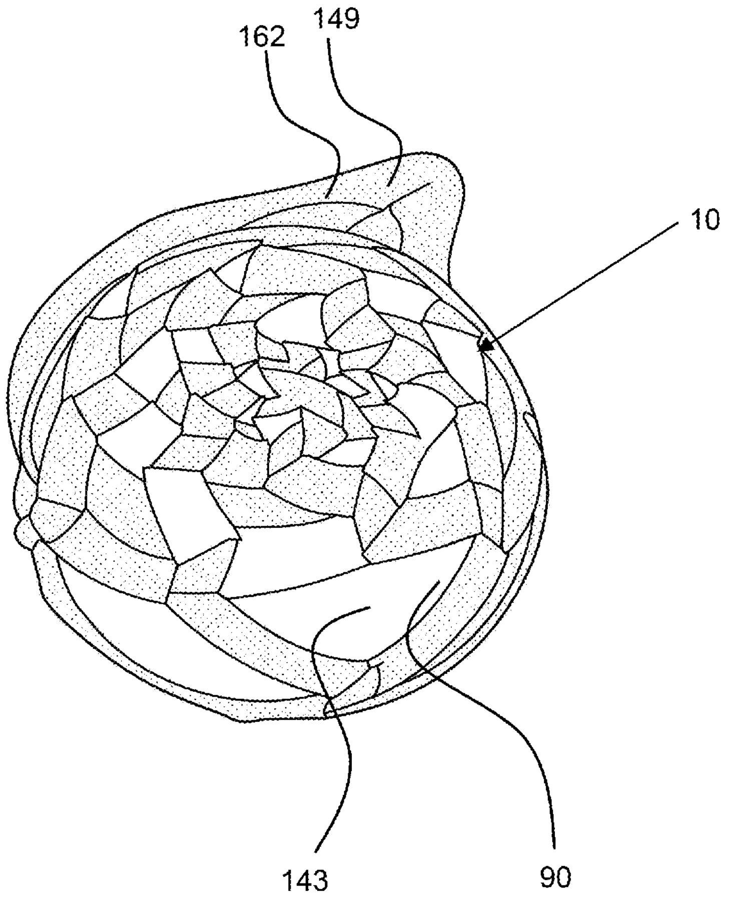
FIG. 46 shows a breast implant configured within a pouch having an exemplary biological compliant scaffold with a differentially compliant geometric pattern of apertures configured for expansion toward a medial side.

As shown in FIG. 46, an exemplary biological compliant scaffold 10 is configured over a breast implant 143 and has a differentially compliant geometric pattern of apertures 93. This biological compliant scaffold 10 may be configured for expansion toward a medial side.

Figure 47:
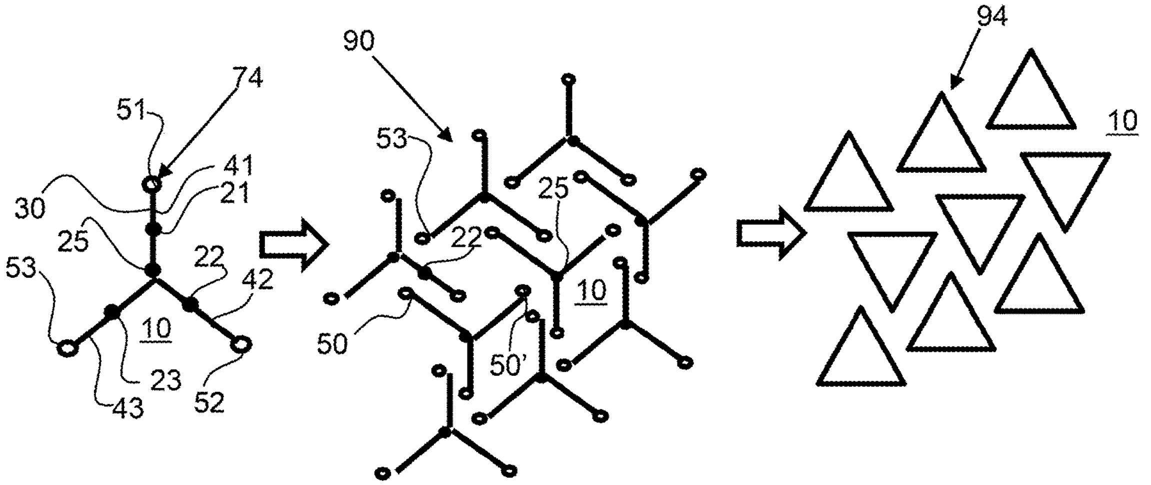
FIG. 47 shows an exemplary geometric pattern of Y-shaped apertures having antinodes configured proximal to a tri-node, or node at the intersection of the first extension, second extension and third extension of the elongated aperture.
Figure 48:
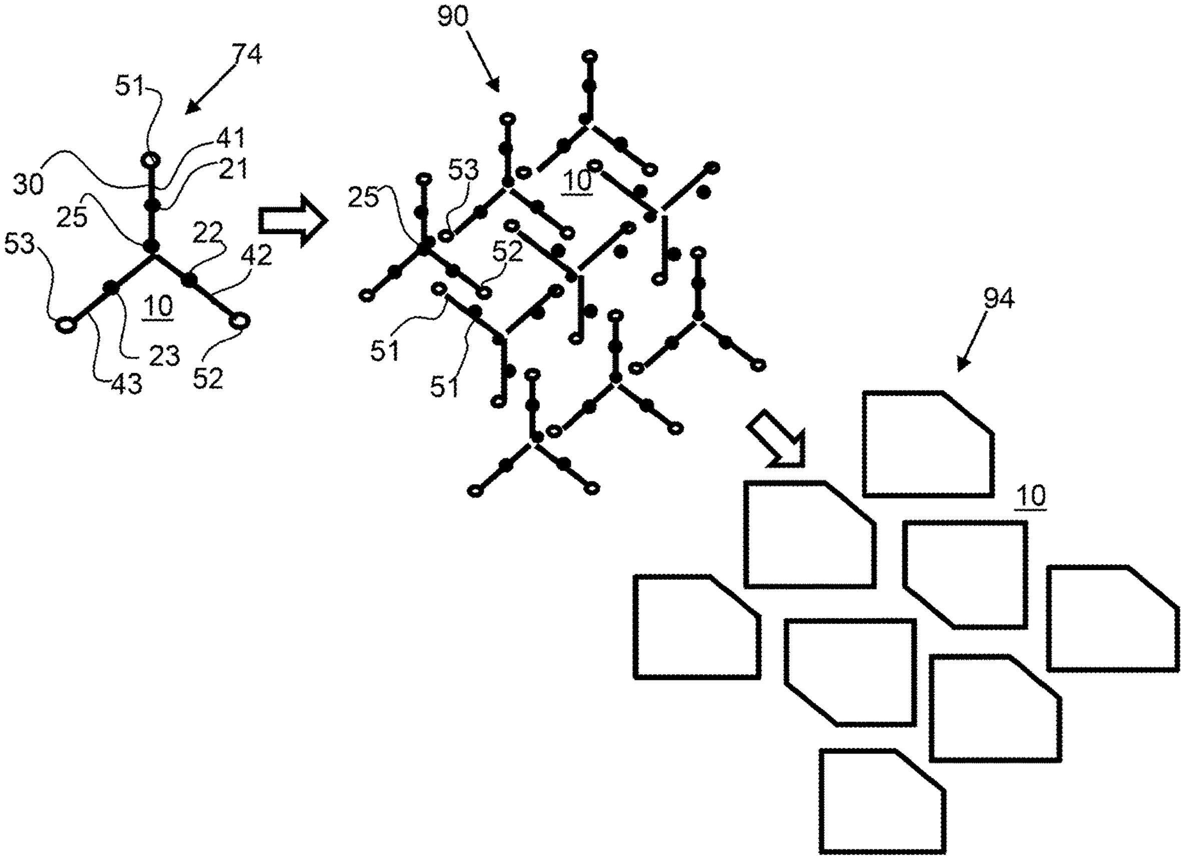
FIG. 48 shows an exemplary geometric pattern of Y-shaped apertures having antinodes configured proximal to a node at the intersection of the first extension, second extension and third extension of the elongated aperture.

As shown in FIGS. 47 to 48, an exemplary geometric pattern of apertures 90 comprises antinodes 50' configured proximal to a tri-node 25, or node at the intersection of the first extension 41, second extension 42 and third extension 43 of the elongated aperture 30. The geometric pattern of apertures 90 also has antinodes 50 configured proximal to second node 22, or node configured along the extension between the tri-node 25 and the antinode 52. The Y-shaped aperture 74 has a first node 21, second node 22 and a third node 23 configured along the first, second and third extensions, respectively. This arrangement of node-antinode pairs enables expansion of the apertures to produce an expanded scaffold 94 or expanded compliant scaffold for compliance to a shape.

Figure 49:
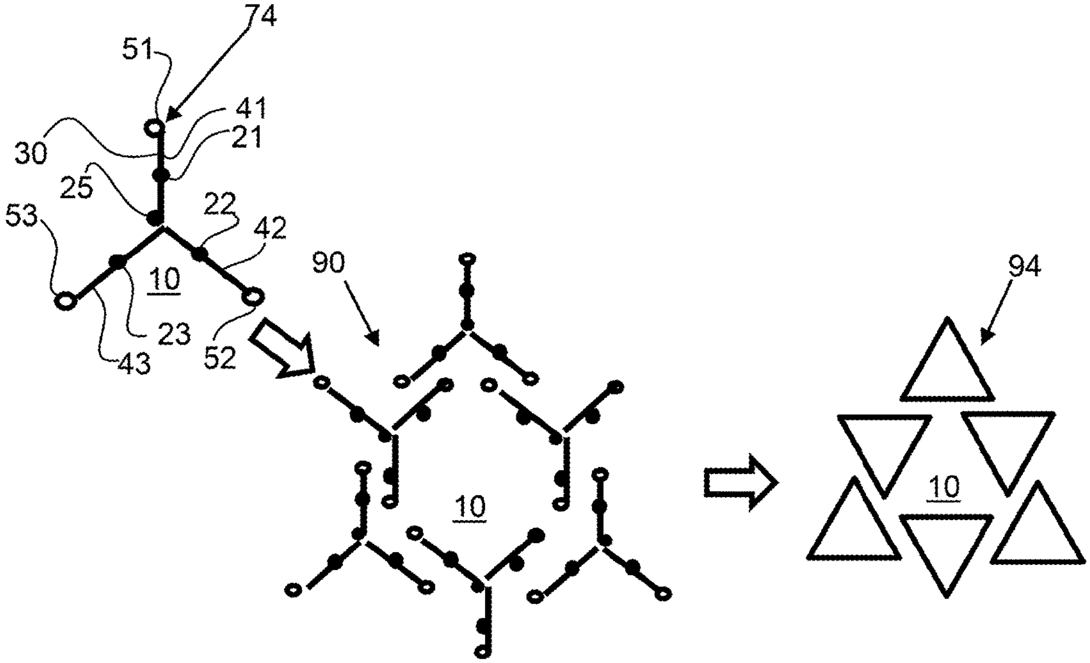
FIG. 49 shows an exemplary geometric pattern of Y-shaped apertures having antinodes configured proximal to a node at the intersection of the first extension, second extension and third extension of the elongated aperture, wherein the geometric pattern form a ring.
Figure 50:
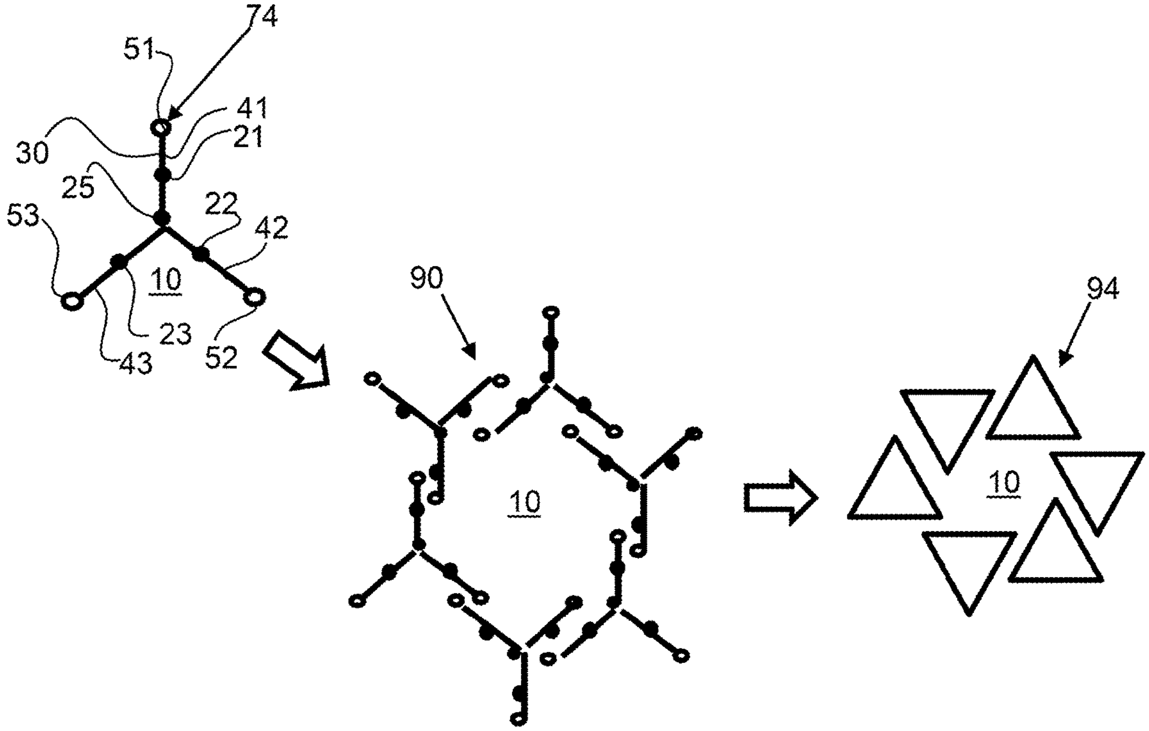
FIG. 50 shows an exemplary geometric pattern of Y-shaped apertures having antinodes configured proximal to a node at the intersection of the first extension, second extension and third extension of the elongated aperture, wherein the geometric pattern form a ring.

As shown in FIGS. 49 and 50, the exemplary geometric pattern of apertures 90 comprises antinodes 51, 52, 53 configured proximal to first node, second node 22 and third node 23 of adjacent elongated Y-shaped aperture 74. This arrangement of node-antinode pairs enables expansion of the apertures to produce an expanded scaffold 94 or expanded compliant scaffold for compliance to a shape.

Figure 51:
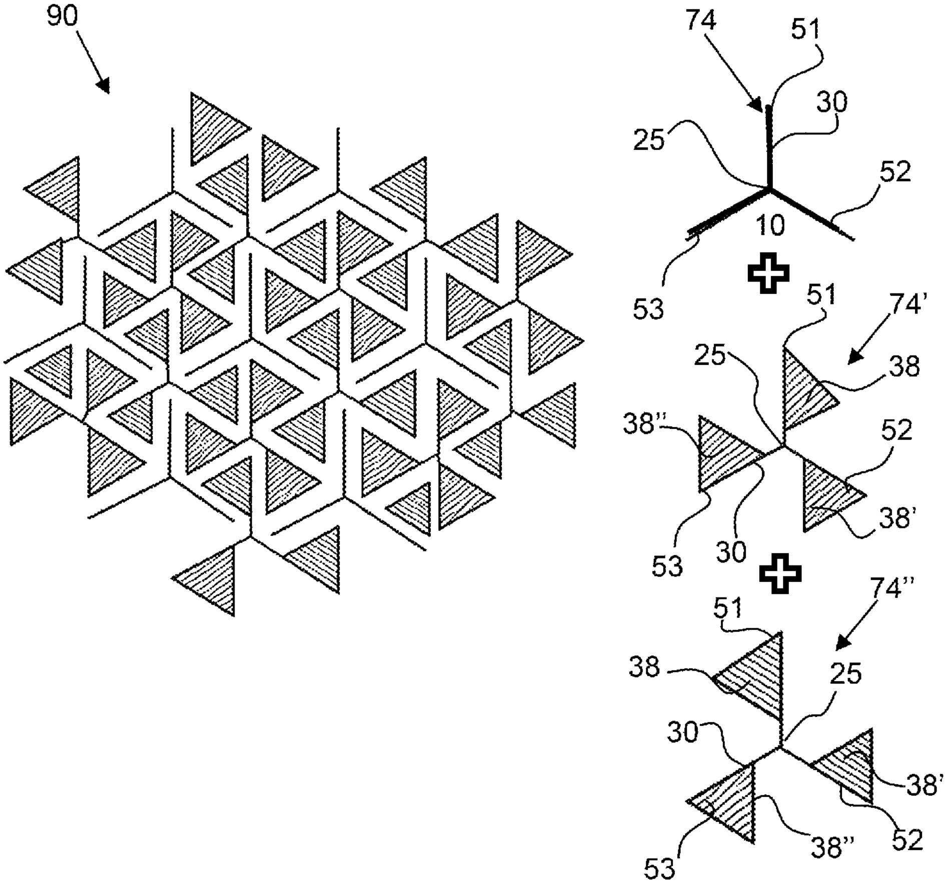
FIG. 51 shows a geometric pattern of apertures that includes Y-shaped apertures having a tri-node at the intersection of the elongated apertures, a second Y-shaped aperture also having a tri-node at the intersection of the elongated apertures and with blanks configured proximal to the antinodes that are triangular in shape and a third Y-shaped aperture also having a tri-node at the intersection of the elongated apertures and with blanks configured proximal to the antinodes that are triangular in shape, but configured in a different orientation from those of the second Y-shaped aperture.

As shown in FIG. 51, a geometric pattern of apertures 90 includes Y-shaped apertures 74 having a tri-node 25 at the intersection of the elongated apertures 30, a second Y-shaped aperture 74' also having a tri-node at the intersection of the elongated apertures and with blanks 38, 38', 38", configured proximal to the antinodes 51, 52, 53 that are triangular in shape and a third Y-shaped aperture 74" also having a tri-node at the intersection of the elongated apertures and with blanks configured proximal to the antinodes 51, 52, 53 that are triangular in shape, but configured in a different orientation from those of the second Y-shaped aperture. The blanks are triangular in shape with one side of the triangle being aligned with the elongated aperture, or an extension of the elongated aperture. This geometric pattern of apertures may be used to form a 3-dimensional wire frame for a stent.

Figure 52:
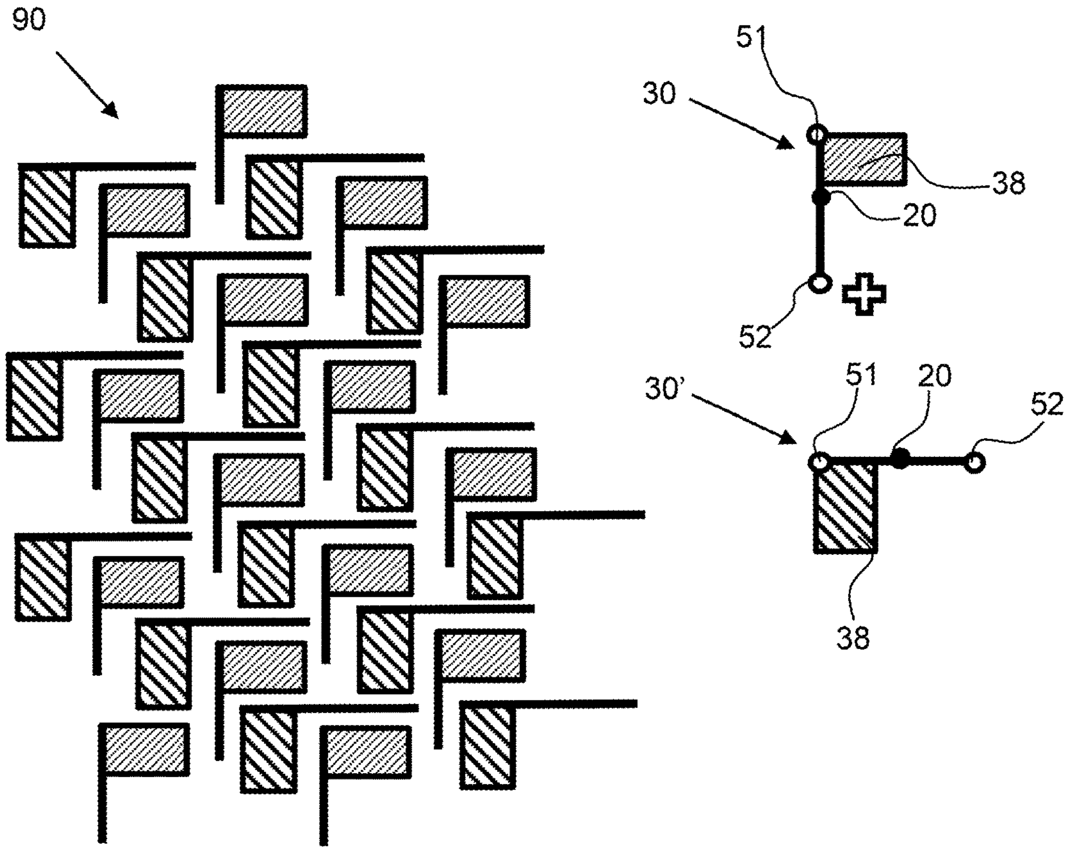
FIG. 52 shows a geometric pattern of apertures that includes elongated apertures each having a first antinode, second antinode, and node configured between the two antinodes and a blank configured proximal to the first antinodes

As shown in FIG. 52, a geometric pattern of apertures 90 includes elongated apertures 30, 30' each having a first antinode 51, second antinode 52, and a node 20 configured between the two antinodes and a blank configured proximal to the first antinodes. The blanks are rectangular in shape with one side being aligned with the elongated aperture. This geometric pattern of apertures may be used to form a 3-dimensional wire frame for a stent.

Figure 53:
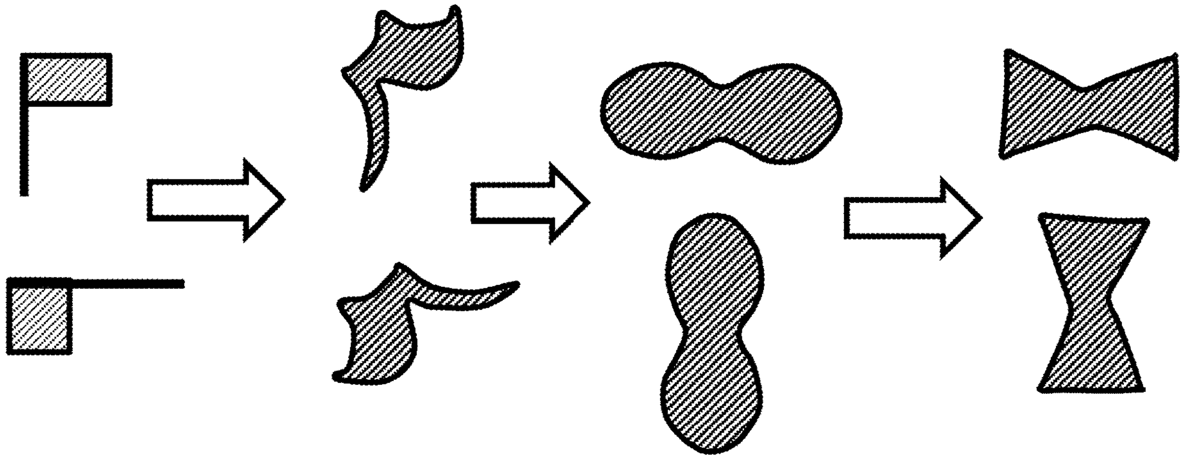
FIG. 53 shows a partially and fully expanded aperture from the elongated apertures used to form the geometric apertures in FIG. 52.

FIG. 53 shows a partially and fully expanded apertures from the elongated apertures used to form the geometric apertures in FIG. 52.

Figure 54:
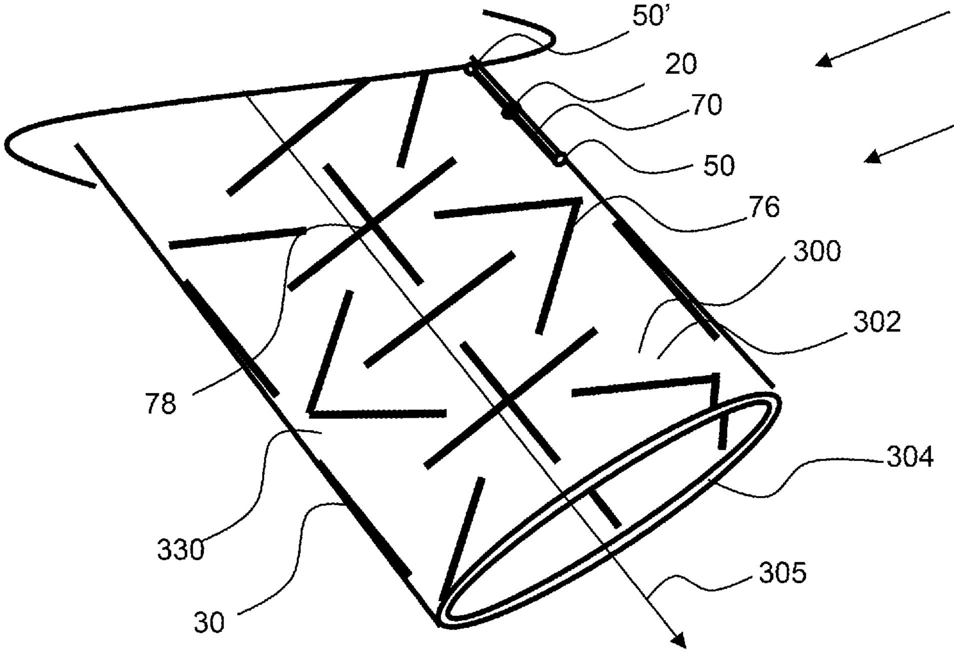
FIG. 54 shows a perspective view of a tube compliant scaffold with a geometric pattern of apertures extending through the tube from a first side through to an opposing side.
Figure 55:
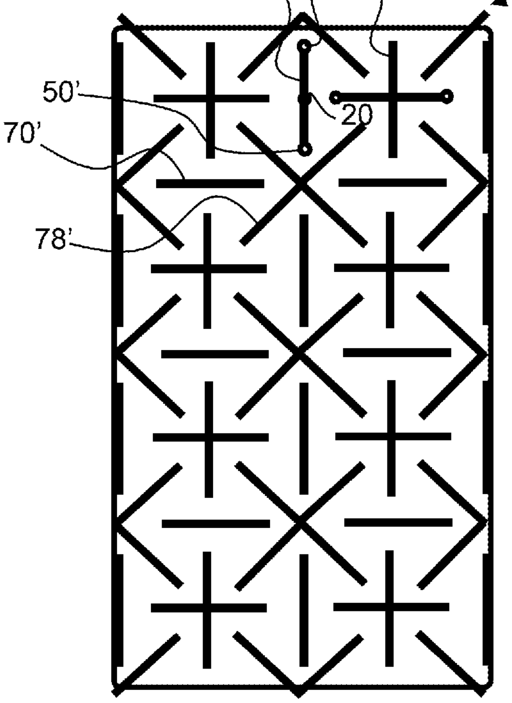
FIG. 55, shows a first side view of a tube compliant scaffold with a geometric pattern including two columns of cross-shaped apertures on a side of the tube, wherein a side of the tube would be produced when the tube is flattened to produce a first side an opposing second side with folds between the sides.

Referring now to FIGS. 54 and 55, an exemplary compliant scaffold 10 is a three-dimensional compliant scaffold 330, a tube 300, having a geometric pattern of apertures 90 configured through said tube 300 or cylinder, from a first 302 side through an opposing second side 304. As shown in FIG. 54 the exemplary geometric pattern of apertures 90 includes a column of cross-shaped apertures 78 configured is series along the length axis of the tube and separated by an elongated aperture 30 or I shaped aperture 70 having a pair of antinodes 50, 50' and a node 20. Skewed apertures 76 are configured between the I shape aperture and also between the cross-shaped apertures 78. This pattern is shown in FIG. 39. As shown in FIG. 55, the tube has two columns of cross shaped apertures on the first side. Again, this pattern extends through the tube and through the second side as well. This geometric pattern of apertures enables expansion of the tube both radially and axially, or along the length axis 305.

Figure 56:
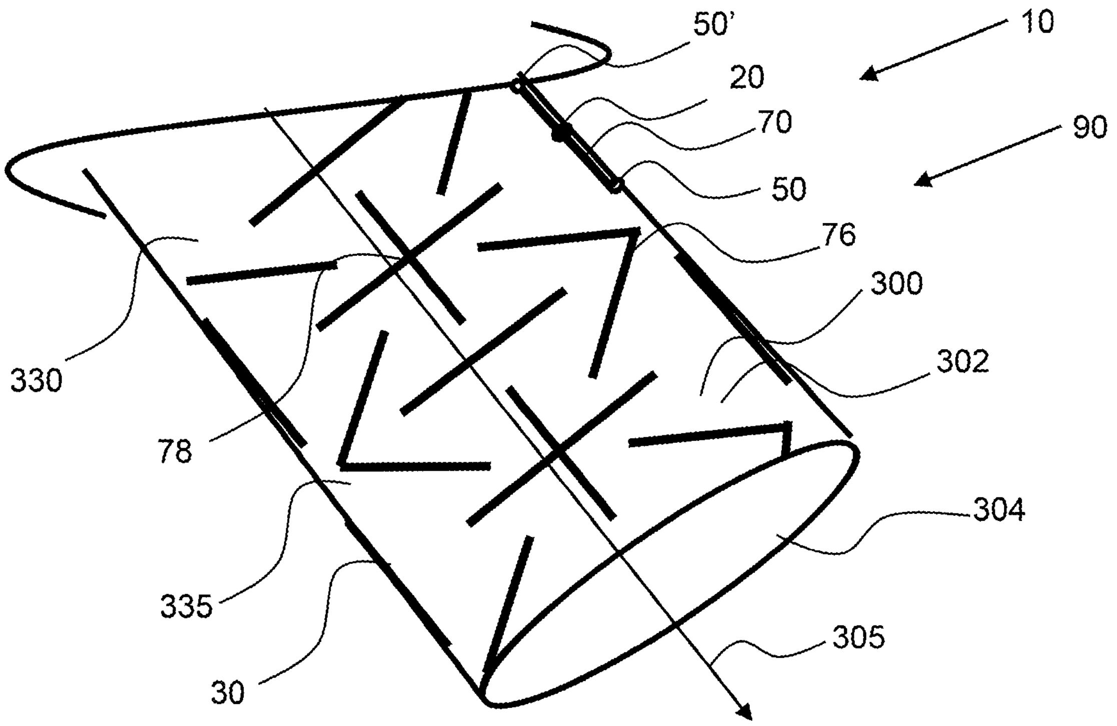
FIG. 56 shows a perspective view of a rod compliant scaffold with a geometric pattern of apertures extending through the rod from a first side to an opposing second side.

As shown in FIG. 56, the same geometric pattern of apertures 90 shown in FIG. 54 is configured through a three-dimensional compliant scaffold 330, a rod shaped 310 compliant scaffold 10. The elongated apertures 30, extend through from one surface, or side of the rod, to the opposing surface or side to form wedges 335 of the three-dimensional scaffold that can move independently while being connected to the other wedges. The apertures extend orthogonally to the surface of the rod. Again, the geometric pattern of apertures includes cross-shaped apertures 78, skewed apertures 76 and I-shaped apertures 70.

Figure 57:
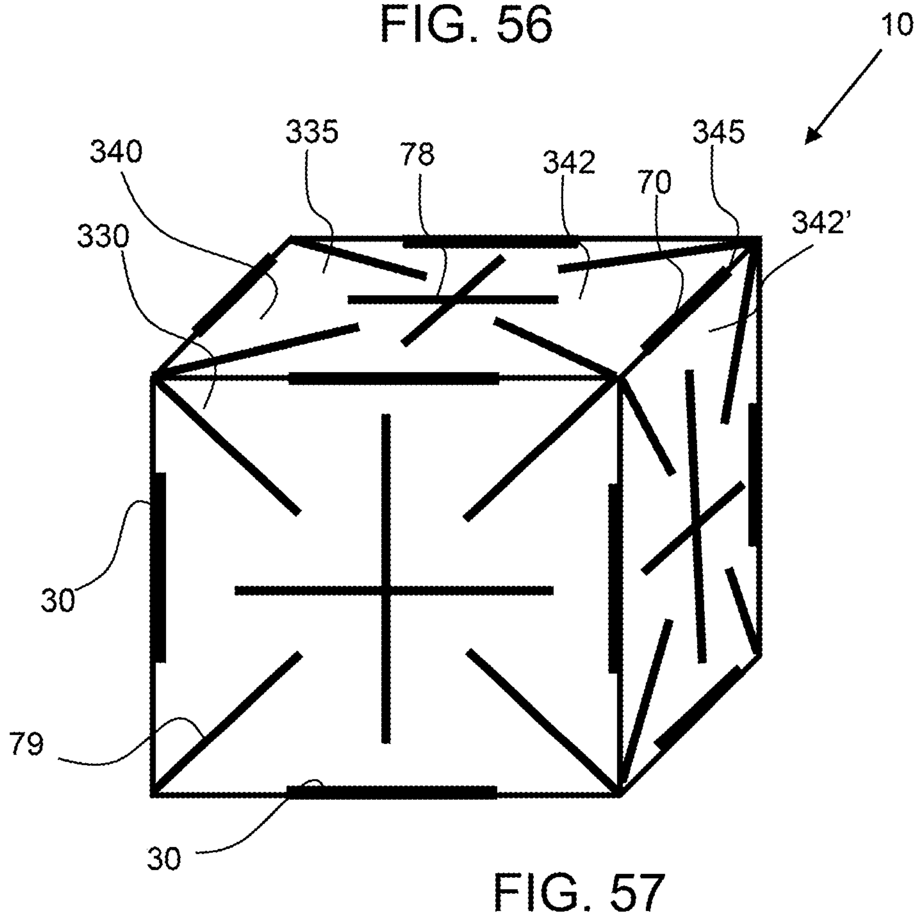
FIG. 57 shows a perspective view of a polyhedron compliant scaffold having with a geometric pattern of apertures extending through the rod from a first side to an opposing second side.

As shown in FIG. 57, a polyhedron compliant scaffold 340 is a three-dimensional compliant scaffold 330, a cube or block. A polyhedron is a three-dimensional shape with flat polygonal faces, straight edges and sharp corners or vertices. A convex polyhedron is the convex hull of finitely many points, not all on the same plane. Cubes and pyramids are examples of convex polyhedra. A compliant scaffold may be a polyhedron or a tube or rod or other solid having curved outer surfaces, or an irregular compliant scaffold having some combination of curved and/or planar surfaces which may include flat polygonal faces. Again, the elongated apertures or any aperture described herein may extend all the way through the compliant scaffold and may extend orthogonal to the surface to an opposing surface. In the case of a square or rectangle, the apertures may extend from one planar surface all the way through the cube to the opposing planar surface. As shown in FIG. 57, the cube or block shaped compliant scaffold has corner apertures 79 that extend from the corner onto one or more of the surfaces of the block. As shown the corner aperture has extensions on each of the sides of the block forming said corner. The block or polyhedron compliant scaffold 340 also has cross-shaped apertures 78 configured through each of the six faces to an opposing face or side, and I shaped apertures along each edge 345 configured between adjacent faces 342 of the polyhedron compliant scaffold 340, such as edge 345 extending between face 342 and face 342'.

Figure 58:
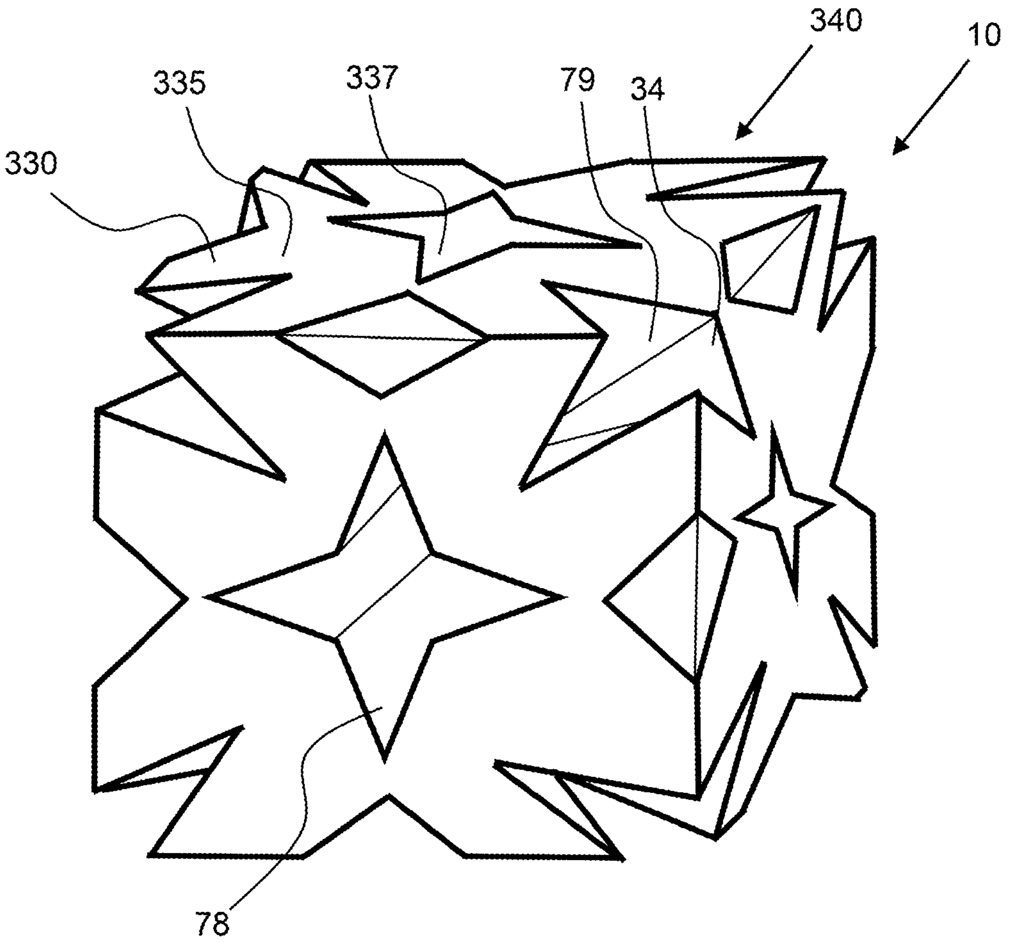
FIG. 58 shows the polyhedron compliant scaffold shown in FIG. 57 expanded.

FIG. 58 shows the polyhedron compliant scaffold 340 shown in FIG. 57 is expanded, wherein the elongated apertures 30 have opened up to enable the polyhedron compliant scaffold 340 to be compliant. The apertures are partially expanded apertures 34 such as the cross-shaped aperture 78 and the corner aperture 79. The wedges 335 of the three-dimensional scaffold 330 can move independently while being connected to the other wedges. In an alternative embodiment, a cube polyhedron compliant scaffold 340 may have apertures that have a width, or gap apertures 337, to allow the compliant scaffold to compress, whereby the apertures shown in FIG. 58 may be made in the compliant scaffold for this purpose. Material of the compliant scaffold 10 may be removed to form these gap apertures 337 or the three-dimensional scaffold 330 may be formed, such as through molding to form these gap apertures 337. Also note that the apertures in polyhedron compliant scaffold 340 may extend only partially into compliant scaffold 10 or may extend into the cube and intersect with one or more other apertures extending into the cube, such as proximal to the center of the cube to produce wedges 335, or portions of the three-dimensional compliant scaffold that can move independently from the other wedges.

Figure 59:
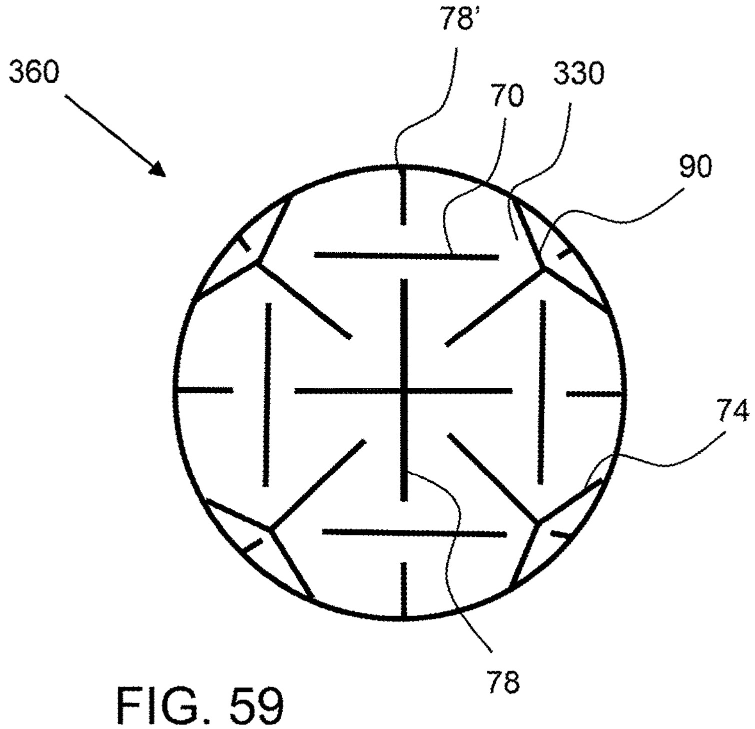
FIG. 59 shows a curved surface compliant scaffold, a sphere, having a geometric pattern of apertures extending through the rod from a first side to an opposing second side.

FIG. 59 shows an exemplary curved surface compliant scaffold 360, a sphere 366, having a geometric pattern of apertures 90 that extend through the sphere to an opposing side. As described herein, the apertures may extend normal to the curved surface through the sphere to the other side. This geometric pattern of apertures includes cross-shaped apertures 78 that are configured in ring around the sphere with I-shaped apertures 70 configured therebetween each of the cross-shaped apertures. Offset and between each of the cross-shaped apertures is a Y-shaped aperture 74 with an extending toward the intersection point of the cross-shaped aperture. The apertures in the curved surface compliant scaffold may extend only partially into the sphere 366 or may extend into the sphere and intersect with one or more other apertures extending into the sphere. For example, all or some of the apertures may extend radially inward toward a center of the sphere and may terminate at the center of the sphere, thereby creating a sphere that can expand radially outward from the center. Also, with reference to FIG. 58, the apertures in the sphere may have a width or compliant scaffold material removed to allow the sphere to compress radially inward.

Figure 60:
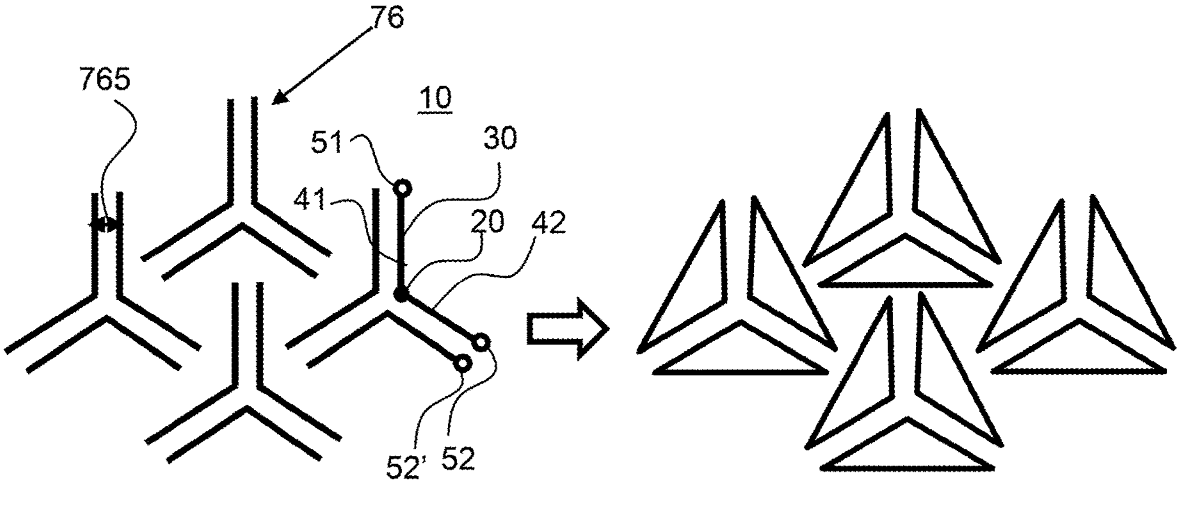
FIG. 60 shows a geometric pattern of skewed elongated apertures that have an arrangement of three skewed elongated apertures offset an offset distance from each other and then arranged with the antinodes at the end of parallel extensions extending toward and being proximal to the node or nodes of an adjacent set of three skewed elongated apertures.

As shown in FIG. 60, a geometric pattern of skewed elongated apertures 76 has an arrangement of three skewed elongated apertures offset an offset distance 765 from each other and then arranged with the antinodes 52, 52' at the end of parallel extensions 42 extending toward and being proximal to the node or nodes of an adjacent set of three skewed elongated apertures. The elongated apertures open up into triangular openings, as shown the compliant scaffold is expanded.

Figure 61:
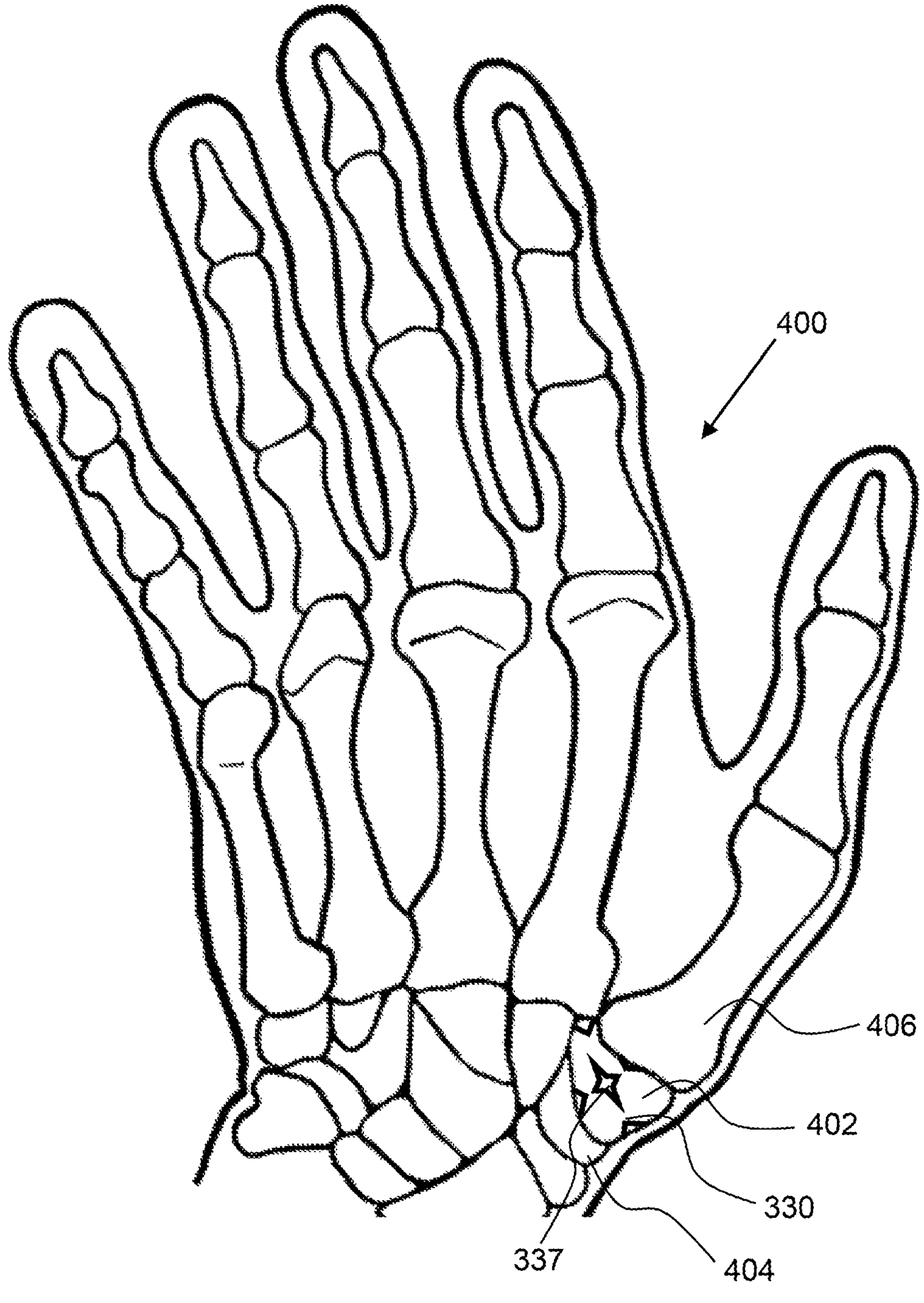
FIG. 61 shows the bones of the hand with the trapezium bone being a compliant scaffold with a plurality of elongated apertures in said compliant scaffold that form a geometric pattern of elongated apertures.

As shown in FIG. 61, the bones of the hand 400 include the trapezium 402 being a three-dimensional compliant scaffold 330 with a plurality of elongated gap apertures 337 in said compliant scaffold that form a geometric pattern of elongated apertures. The gap apertures have material removed from between the nodes to enable the gap aperture and the three-dimensional compliant scaffold to compress. The trapezium 402 is configured between the third metatarsal 406 and the scaphoid 404 and may be compressed during extension of the thumb away from the fingers.

Figure 62:
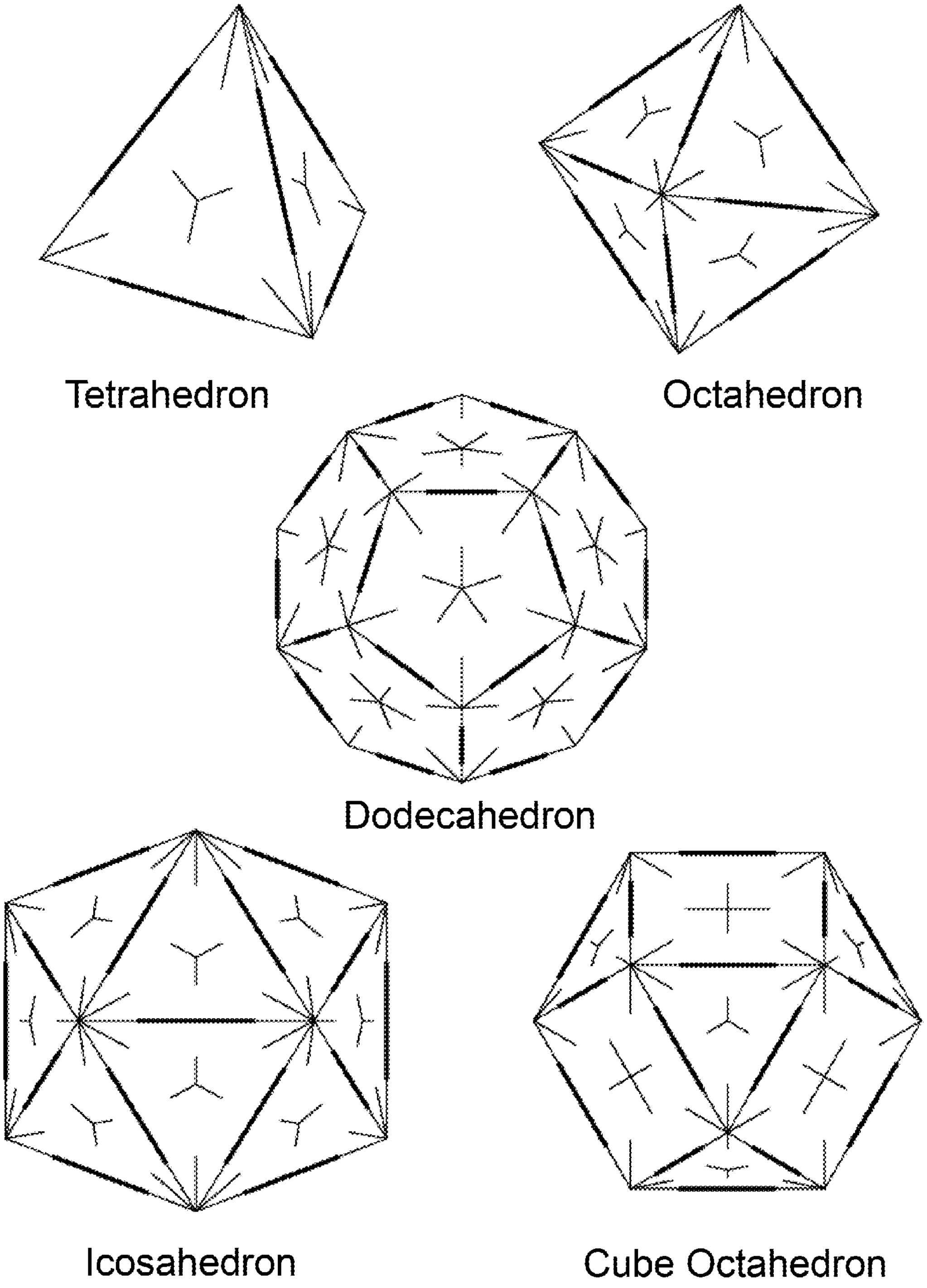
FIG. 62 shows diagrams of various polyhedrons that are three-dimensional compliant scaffolds having a plurality of elongated apertures.

FIG. 62 shows diagrams of various polyhedrons that are three-dimensional compliant scaffolds having a plurality of elongated apertures It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A compliant scaffold comprising:

a) a plurality of elongated apertures in said compliant scaffold that forms a geometric pattern, each of said plurality of elongated apertures comprising;

i) a pair of nodes; and ii) a pair of antinodes;

wherein the pair of nodes are centrally located along the elongated aperture with a first node on a first side of the elongated aperture and a second node on a second side of the elongated aperture; and wherein a first antinode is configured on a first antinode end of the elongated aperture and a second antinode is configured on a second antinode end of the elongated aperture;

b) a plurality of geometric shapes having a bounded perimeter formed by said plurality of elongated apertures;

wherein upon biaxially expanding the compliant scaffold, the first and second nodes separate from each other and wherein a distance between the antinodes contracts to form an arrangement of tessellated apertures in the compliant scaffold;

wherein the plurality of elongated apertures forms said geometric pattern with a substantial portion of elongated apertures configured with the antinodes proximal to one of said pair of nodes of a separate elongated aperture; wherein the antinodes are closer to said one of said pair of nodes than to any other antinode; and wherein the plurality of elongated apertures comprises expanded elongated apertures;

wherein the compliant scaffold comprises biological material;

wherein the geometric pattern of elongated apertures comprises I-shaped apertures; and wherein the geometric pattern of elongated apertures comprises cross-shaped apertures.

2. The compliant scaffold of claim 1, wherein the compliant scaffold comprises a biological material derived from a living organism.

3. The compliant scaffold of claim 1, wherein the geometric pattern of elongated apertures is differentially compliant, wherein gap distances between antinodes and nodes varies over the geometric pattern to produce differential compliance.

4. The compliant scaffold of claim 3, wherein the geometric pattern of elongated apertures comprises rows of elongated apertures and wherein the spacing between the apertures is substantially uniform over the geometric pattern while said gap distances between antinodes and nodes vary over the geometric pattern to produce differential compliance.

5. The compliant scaffold of claim 3, wherein the geometric pattern of elongated apertures comprises Y-shaped apertures.

6. The compliant scaffold of claim 3, wherein the length of the elongated apertures changes over the geometric pattern of elongated apertures.

7. The compliant scaffold of claim 6, wherein the gap distance between nodes and antinodes is progressively larger from a center of the geometric pattern of elongated apertures, and wherein the compliant scaffold is configured to produce a dome shape.

8. The compliant scaffold of claim 1, wherein the I-shaped apertures extend between the cross shaped apertures.

9. The compliant scaffold of claim 1, wherein the geometric pattern of elongated apertures comprises cross-shaped apertures are arranged in rows.

10. The compliant scaffold of claim 1, wherein at least one of the plurality of elongated apertures comprises a blank that extends from the elongated aperture into the compliant material.

11. The compliant scaffold of claim 10, wherein the blank is a triangular shaped blank.

12. The compliant scaffold of claim 11, wherein the triangular shaped blank has a side that extends along the elongated aperture.

13. The compliant scaffold of claim 12, wherein the triangular shaped blank has a side that terminates at an end of the elongated aperture.

14. The compliant scaffold of claim 12, wherein the elongated aperture is a Y-shaped aperture and wherein each of the extensions of the Y-shaped aperture has a blank with a side that extends along the extension.

15. The compliant scaffold of claim 14, wherein each of the triangular shaped blanks has a side that terminates at an end of the extension.

* * * * *